United States Patent
Luesch et al.

(10) Patent No.: US 9,815,852 B2
(45) Date of Patent: Nov. 14, 2017

(54) MACROCYCLIC COMPOUNDS AND METHODS OF TREATMENT

(71) Applicant: University of Florida Research Foundation, Inc., Gainesville, FL (US)

(72) Inventors: Hendrik Luesch, Gainesville, FL (US); Jiyong Hong, Durham, NC (US)

(73) Assignees: University of Florida Research Foundation, Incorporated, Gainesville, FL (US); Duke University, Durham, NC (US)

( * ) Notice: Subject to any disclaimer, the term of this patent is extended or adjusted under 35 U.S.C. 154(b) by 0 days.

(21) Appl. No.: 15/320,870

(22) PCT Filed: Jun. 25, 2015

(86) PCT No.: PCT/US2015/037794
§ 371 (c)(1),
(2) Date: Dec. 21, 2016

(87) PCT Pub. No.: WO2015/200699
PCT Pub. Date: Dec. 30, 2015

(65) Prior Publication Data
US 2017/0197988 A1     Jul. 13, 2017

Related U.S. Application Data

(60) Provisional application No. 62/017,641, filed on Jun. 26, 2014.

(51) Int. Cl.
| | | |
|---|---|---|
| *C07D 513/14* | (2006.01) | |
| *A61K 31/429* | (2006.01) | |
| *A61K 45/06* | (2006.01) | |

(52) U.S. Cl.
CPC .......... *C07D 513/14* (2013.01); *A61K 31/429* (2013.01); *A61K 45/06* (2013.01)

(58) Field of Classification Search
CPC ............................ C07D 513/14; A61K 31/429
See application file for complete search history.

(56) References Cited

U.S. PATENT DOCUMENTS

| | | | | |
|---|---|---|---|---|
| 8,129,418 B2 * | 3/2012 | Luesch | ................ | C07D 513/18 514/366 |
| 8,217,076 B2 * | 7/2012 | Williams | ............. | C07D 498/18 514/539 |
| 8,759,512 B2 * | 6/2014 | Luesch | ................ | C07D 513/16 540/455 |
| 9,023,875 B2 * | 5/2015 | Luesch | ................ | C07D 513/18 514/366 |
| 9,186,402 B2 * | 11/2015 | Williams | ............. | C07D 498/18 |

FOREIGN PATENT DOCUMENTS

| | | |
|---|---|---|
| WO | WO 2009/105284 A1 | 8/2009 |
| WO | WO 2010/009334 A1 | 1/2010 |

OTHER PUBLICATIONS

International Search Report and Written Opinion dated Mar. 31, 2016 for Application No. PCT/US2015/037794.
Bhansali et al., Synthesis and biological evaluation of largazole analogues with modified surface recognition cap groups. Eur J Med Chem. Oct. 30, 2014;86:528-41. doi:10.1016/j.ejmech.2014.09.009.
Kim et al., Evaluation of class I HDAC isoform selectivity of largazole analogues. Bioorg Med Chem Lett. Aug. 15, 2014;24(16):3728-31. doi:10.1016/j.bmcl.2014.07.006. Supplementary Data Included.
Ying et al., Total synthesis and molecular target of largazole, a histone deacetylase inhibitor. J Am Chem Soc. Jul. 2, 2008;130(26):8455-9. doi: 10.1021/ja8013727.

* cited by examiner

*Primary Examiner* — Golam M M Shameem
(74) *Attorney, Agent, or Firm* — Wolf, Greenfield & Sacks, P.C.

(57) ABSTRACT

The instant invention describes macrocyclic compounds having therapeutic activity, and methods of treating disorders such as cancer, tumors and cell proliferation related disorders.

10 Claims, No Drawings

MACROCYCLIC COMPOUNDS AND METHODS OF TREATMENT

CROSS REFERENCE TO RELATED APPLICATIONS

This application is the U.S. National Stage, pursuant to 35 U.S.C. §371, of U.S. International Application No. PCT/US2015/037794, filed Jun. 25, 2015, designating the United States and published on Dec. 30, 2015 as Publication WO 2015/200699, which claims the benefit of U.S. Provisional Patent Application Ser. No. 62/017,641 filed Jun. 26, 2014, which applications are expressly incorporated by reference herein

STATEMENT OF RIGHTS TO INVENTIONS MADE UNDER FEDERALLY SPONSORED RESEARCH

The invention was made with government support under Heath Grant No. CA138544 awarded by the National Institutes of Health. The government has certain rights in the invention.

BACKGROUND

The identification of new pharmacophores is of paramount biomedical importance and natural products have recently been regaining attention for this endeavor.[1] This renaissance is closely tied to the successful exploitation of the marine environment which harbors unmatched biodiversity that is presumably concomitant with chemical diversity.[2] In particular, marine cyanobacteria are prolific producers of bioactive secondary metabolites,[3] many of which are modified peptides or peptide-polyketide hybrids with promising antitumor activities, such as dolastatin 10,[4] curacin A,[5] and apratoxin A.[6] As a result of ongoing investigations to identify new drug leads from cyanobacteria in Florida, we report here the structure determination and preliminary biological characterization of a marine cyanobacterial metabolite with novel chemical scaffold and nanomolar antiproliferative activity. These findings provide new alternatives to address unmet needs in the treatment of proliferation diseases and disorders. The compounds herein are also now found to mediate histone deacetylase (HDAC) processes (e.g., inhibition) and as such are useful for treating diseases, disorders, or symptoms thereof mediated by inhibition of histone deacetylase (HDAC). These findings provide new alternatives to address unmet needs in the treatment of HDAC mediated diseases and disorders.

BRIEF SUMMARY OF THE INVENTION

The invention is directed towards macrocyclic compounds, and methods of treating disease and disorders, including proliferation diseases and disorders, and HDAC mediated diseases and disorders, by use of the compounds and compositions thereof.

The invention is directed towards macrocyclic compounds, methods of modulating proliferation activity, and methods of treating proliferation disease and disorders. In one embodiment, the invention provides a compound according to Formulae I or II:

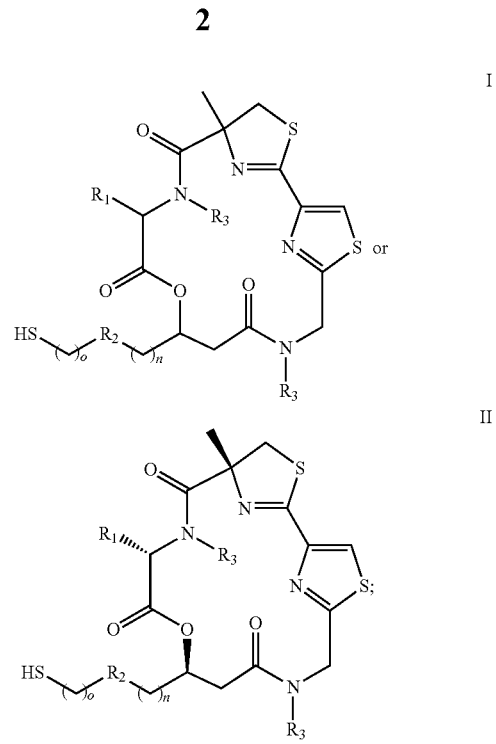

wherein:
each $R_1$ is independently optionally substituted arylalkyl, optionally substituted heteroarylalkyl, optionally substituted carboxyalkyl, or optionally substituted aminoalkyl;
each $R_2$ is independently optionally substituted alkenylene, optionally substituted arylene, or optionally substituted heteroarylene;
each $R_3$ is independently H, optionally substituted alkyl, C(O)OR, or C(O)NRR;
each R is independently H or optionally substituted alkyl;
each n is 0, 1, 2, or 3; and
each o is 0, 1, 2, or 3;
and pharmaceutically acceptable salts, solvate, or hydrate thereof.

Another aspect is a compound of formulae I or II herein, wherein each $R_2$ is independently optionally substituted alkenylene

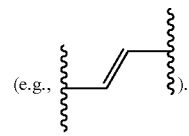

Another aspect is a compound of formulae I or II herein, wherein each $R_2$ is independently optionally substituted alkenylene

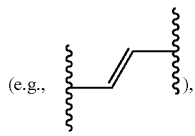

each $R_3$ is H, each n is 0, and each o is 2.
Another aspect is a compound of formulae I or II herein, wherein each $R_2$ is

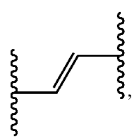 [SMILES: */C=C/*]
each $R_3$ is H, each n is 0, and each o is 2.
Another aspect is a compound of formulae I or II, wherein the compound is selected from the group consisting of:
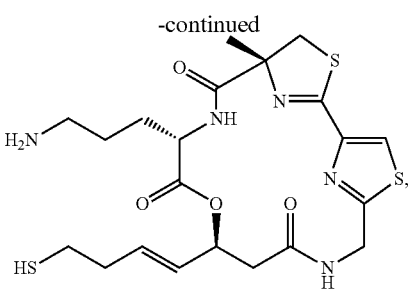
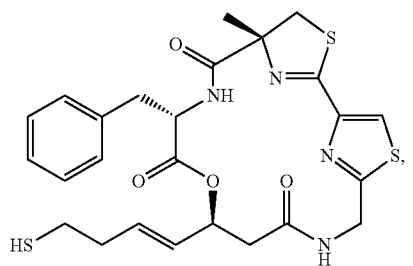
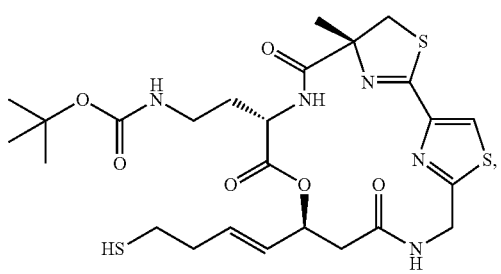
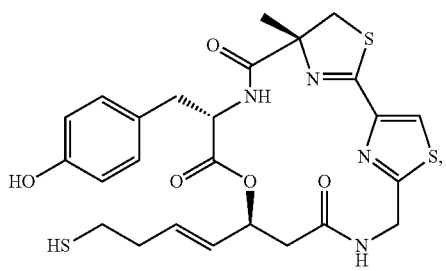
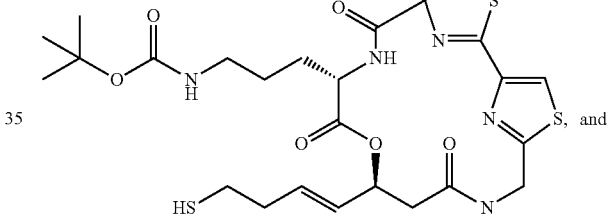
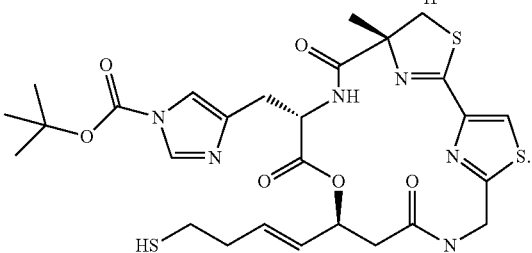
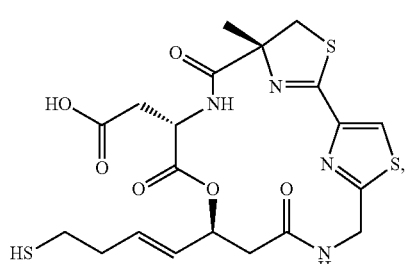
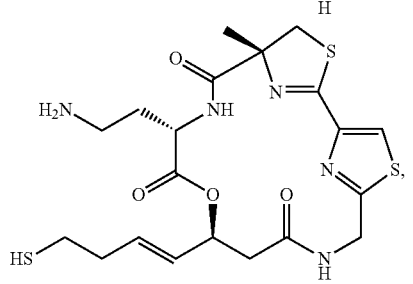
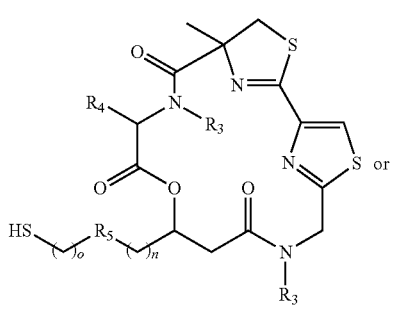
Another aspect is a compound according to Formulae III or IV:
III -continued

IV

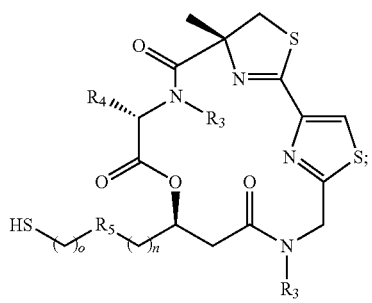

wherein:

each $R_3$ is independently H, optionally substituted alkyl, C(O)OR, or C(O)NRR;

each R is independently H or optionally substituted alkyl;

each $R_4$ is independently H or optionally substituted alkyl;

each $R_5$ is independently optionally substituted arylene or optionally substituted heteroarylene;

each n is 0, 1, 2, or 3; and each o is 0, 1, 2, or 3;

and pharmaceutically acceptable salts, solvate, or hydrate thereof.

Another aspect is a compound of formulae III or IV, wherein $R_4$ is alkyl (e.g., isopropyl).

Another aspect is a compound of formulae III or IV, wherein the compound is selected from the group consisting of:

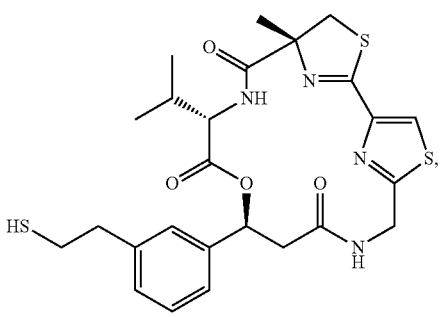

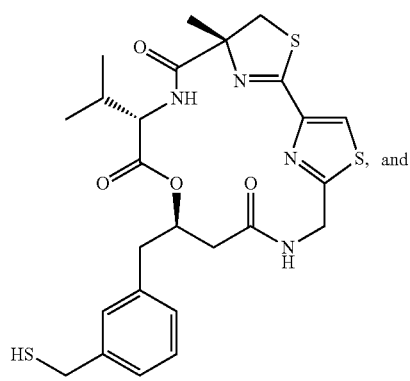

-continued

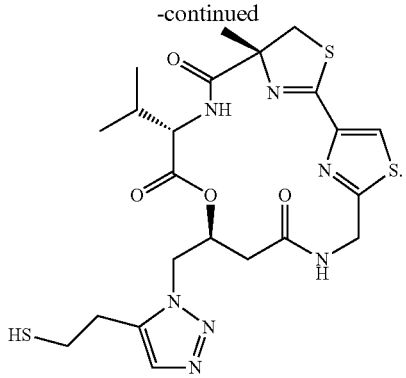

Another aspect is a compound of any of the formulae herein (e.g., formulae I-IV) wherein, $R_1$ and/or $R_4$ is independently optionally substituted arylalkyl or optionally substituted heteroarylalkyl. In another aspect, the optionally substituted arylalkyl is optionally substituted phenylalkyl. In another aspect, the optionally substituted heteroarylalkyl is an optionally substituted (5-membered heteroaryl)alkyl (e.g., imidazolylalkyl). In another aspect, $R_1$ and/or $R_4$ is independently

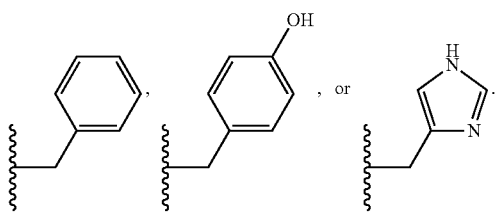

Another aspect is a compound of formulae III or IV, wherein each $R_5$ is independently optionally substituted phenylene or an optionally substituted 5-membered heteroarylene (e.g., triazolylene). In another aspect, each $R_5$ is independently

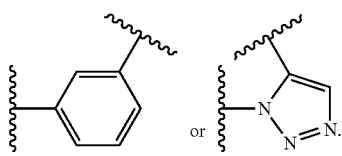 [SMILES: *c1cccc(*)c1 ; *c1cnnn1*]

Another aspect is a compound of any of the formulae herein (e.g., formulae I-IV), wherein the compound is identified as a class I selectective HDAC inhibitor (i.e., having a lower $IC_{50}$ activity value against at least one HDAC1, HDAC2, HDAC3, and HDAC8 (i.e., class I HDACs) than the $IC_{50}$ activity values against any of the class II or class III HDACs).

Another aspect is a compound of any of the formulae herein (e.g., formulae I-IV), wherein the compound is identified as exhibiting less inhibitory activity against HDAC8 than against the other class I HDACs (i.e., having a lower $IC_{50}$ activity value against at least one of HDAC1, HDAC2, and HDAC3 than the $IC_{50}$ activity value against HDAC8).

Another aspect is a compound of any of the formulae herein (e.g., formulae I-IV), wherein the compound is identified as being a selective HDAC1 inhibitor (i.e., having a lower $IC_{50}$ activity value against HDAC1 than against any of the other HDACs).

In certain instances, the compounds of the invention are selected from the following having the structure:
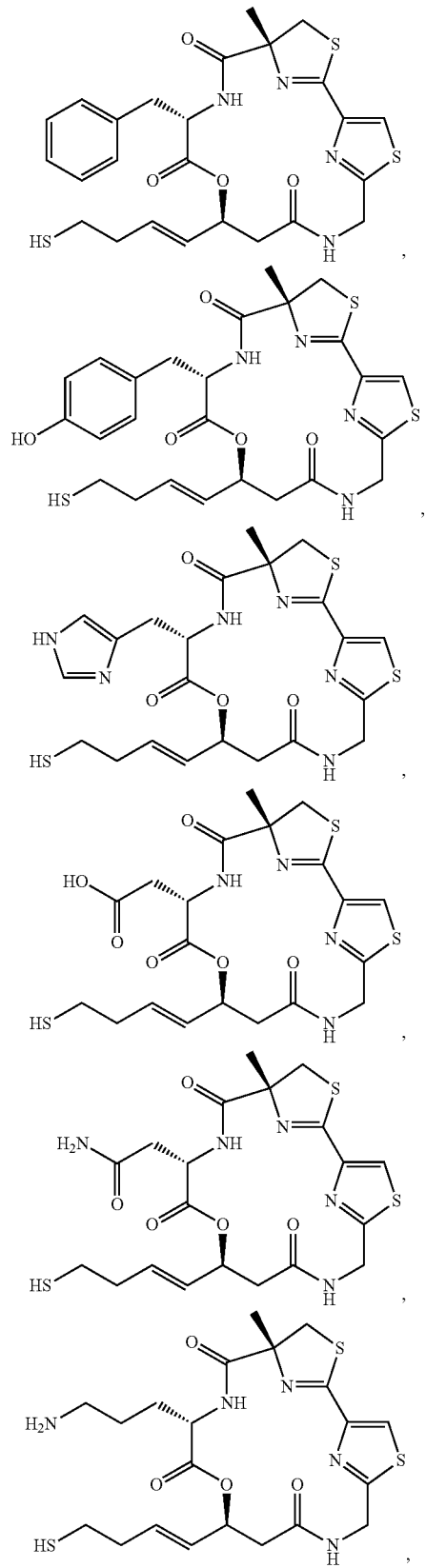
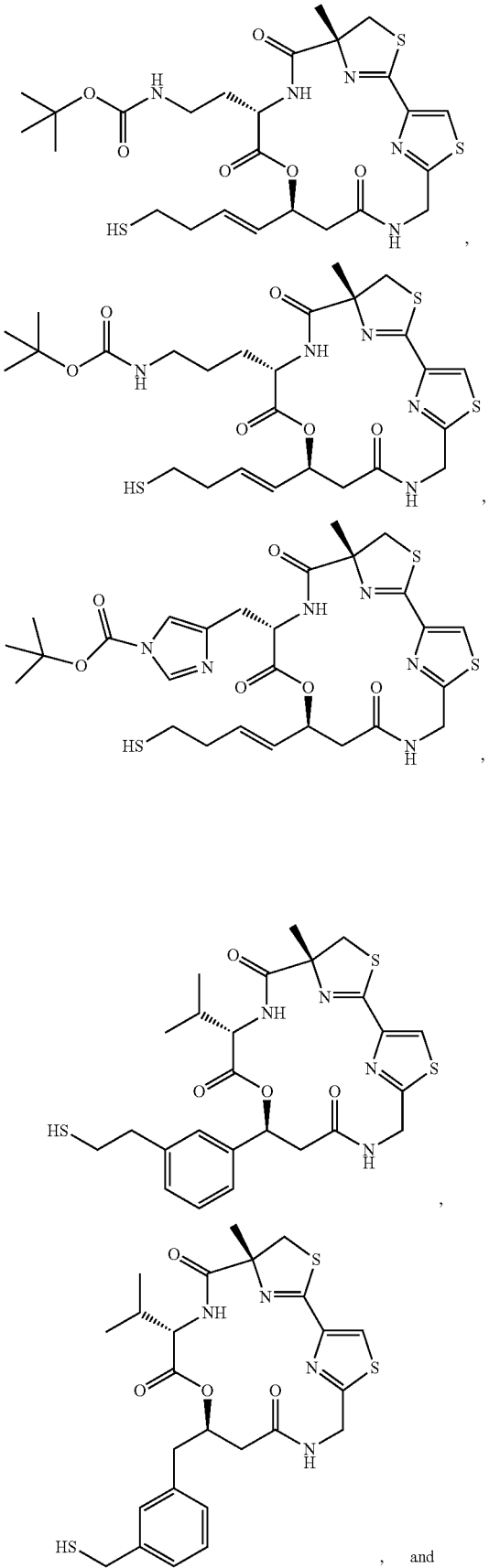

-continued

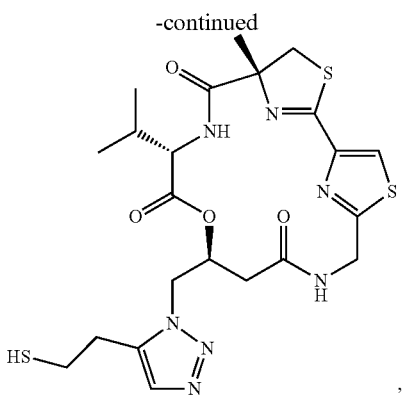

,

In another aspect, the invention provides a pharmaceutical composition comprising the compound of any of the formulae presented herein (e.g., formulae I-IV) and a pharmaceutically acceptable carrier.

In other aspects, the invention provides a method of treating a disease, disorder, or symptom thereof in a subject, comprising administering to the subject a compound of any of the formulae herein (e.g., formulae I-IV). In another aspect, the compound is administered in an amount and under conditions sufficient to ameliorate the disease, disorder, or symptom thereof in a subject.

In other aspects, the invention provides a method of modulating HDAC activity in a subject, comprising contacting the subject with a compound of any of the formulae herein (e.g., formulae I-IV), in an amount and under conditions sufficient to modulate HDAC activity. In another aspect, the modulation is inhibition.

In other aspects, the invention provides a method of modulating the proliferation activity in a subject, comprising contacting the subject with a compound of any of the formulae herein (e.g., formulae I-IV), in an amount and under conditions sufficient to modulate proliferation activity.

In one aspect, the invention provides a method of treating a subject suffering from or susceptible to a proliferation related disorder or disease, comprising administering to the subject an effective amount of a compound or pharmaceutical composition of a compound of any of the formulae herein (e.g., formulae I-IV).

In another aspect, the invention provides a method of treating a subject suffering from or susceptible to a proliferation related activity related disorder or disease, wherein the subject has been identified as in need of treatment for a proliferation related disorder or disease, comprising administering to said subject in need thereof, an effective amount of a compound or pharmaceutical composition of a compound of any of the formulae herein (e.g., formulae I-IV), such that said subject is treated for said disorder.

In another aspect, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of a compound of any of the formulae herein (e.g., formulae I-IV), such that cell proliferation in said subject is modulated (e.g., down regulated). In another aspect, the compounds delineated herein preferentially target cancer cells over nontransformed cells.

In a specific aspect, the invention provides a method of treating cancer, tumor growth, cancer of the colon, breast, bone, brain and others (e.g., osteosarcoma, neuroblastoma, colon adenocarcinoma), comprising administering to said subject in need thereof, an effective amount of a compound delineated herein (e.g., formulae I-IV), and pharmaceutically acceptable salts thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma).

In another aspect, the invention provides a method of inhibiting histone deacetylase (HDAC) in a subject in need thereof comprising administering to said subject, an effective amount of a compound delineated herein (e.g., formulae I-IV), and pharmaceutically acceptable salts thereof.

In another aspect, the invention provides a method of treating diseases, disorders, or symptoms thereof mediated by inhibition of histone deacetylase (HDAC) in a subject in need thereof comprising administering to said subject, an effective amount of a compound delineated herein (e.g., formulae I-IV), and pharmaceutically acceptable salts thereof. Recently, HDAC inhibitors have been found to ameliorate progression of the spinal muscular atrophy (SMA) motor neuron disease and the Huntington disease mouse models. The neuroprotective role of HDAC inhibitors seems to extend to other diseases that share mechanisms of oxidative stress, inflammation and neuronal cell apoptosis. HDAC inhibitors also have widespread modulatory effects on gene expression within the immune system and have been used successfully in the lupus and rheumatoid arthritis autoimmune disease models. Recently, the efficacy of the HDAC inhibitor Trichostatin A was established in ameliorating disease in the multiple sclerosis (MS) animal model, experimental autoimmune encephalomyelitis (EAE). In aspects, the compounds herein are useful to treat MS, an autoimmune, demyelinating and degenerative disease of the human central nervous system (CNS). In aspects the compounds herein are useful to treat stroke. In other aspects, the HDAC inhibitor compounds are useful to treat or prevent memory loss, for inducing neurogenesis, for enhancing memory retention, for enhancing memory formation, for increasing synaptic potential or transmission, or for increasing long term potentiation (LTP).

In another aspect, the invention provides a method of treating diseases, disorders, or symptoms in a subject in need thereof comprising administering to said subject, an effective amount of a compound delineated herein (e.g., formulae I-IV), and pharmaceutically acceptable salts thereof. Such methods are useful for treating memory loss, inducing neurogenesis, enhancing memory retention, enhancing memory formation, increasing synaptic potential or transmission, or increasing long term potentiation (LTP).

In another aspect, the compounds of any of the formulae herein (e.g., formulae I-IV) are compounds having class I HDAC selectivity, thus they are useful as anticancer agents; and furthermore having selectivity for class I HDAC versus class II HDAC also provides a more desirable therapeutic profile as it is indicated that inhibition of certain specific class II HDACs may have undesirable consequences, including for example, promoting cardiac hypertrophy. See, Furumai et al. Cancer Research 2002, 62, 4916-4921; Yurek-George et al. J. Med. Chem. 2007, 50, 5720-5726. Thus, in one aspect, the compounds and methods herein are those wherein the compounds demonstrate selectivity in class I/class II HDAC selectivity (e.g., at least 2-fold, at least 10-fold, at least 100-fold, at least 1000-fold, at least X-fold where X is any number between 1 and 100,000 inclusive).

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

DETAILED DESCRIPTION

Definitions

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.1 mg/kg to about 200 mg/kg, more preferably about 10 mg/kg to about 100 mg/kg of body weight. In other embodiments, the therapeutically effect amount may range from about 1.0 pM to about 500 nM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "heterocyclyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, having at least one nonaromatic ring in a polycyclic ring system, and other rings in the polycyclic ring system may be nonaromatic or aromatic. Heterocyclyl groups may be optionally substituted with one or more substituents. Representative heterocyclyl groups include dihydroquinolinyl, tetrahydroquinazolinyl, dihydrobenzofuranyl and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Compounds of the Invention

Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

The invention is directed towards macrocyclic compounds, and methods of treating disease and disorders using the compounds or compositions thereof delineated herein.

In other aspects, the invention provides a method of treating a subject suffering from or susceptible to HDAC related disorder or disease, wherein the subject has been identified as in need of treatment for a HDAC related disorder or disease, comprising administering to said subject in need thereof, an effective amount of a compound or pharmaceutical composition of a compound of any of the formulae herein (e.g., formulae I-IV), such that said subject is treated for said disorder. Identifying a subject in need of such treatment can be in the judgment of a subject or a health care professional and can be subjective (e.g. opinion) or objective (e.g. measurable by a test or diagnostic method).

In one aspect, the invention provides a method of modulating the proliferation activity of a cell in a subject, comprising contacting the subject with a compound of any of the formulae herein (e.g., formulae I-IV), in an amount and under conditions sufficient to modulate cell proliferation activity.

In one embodiment, the modulation is inhibition.

In another aspect, the invention provides a method of treating a subject suffering from or susceptible to a cell proliferation related disorder or disease, comprising administering to the subject an effective amount of a compound or pharmaceutical composition of a compound of any of the formulae herein (e.g., formulae I-IV).

In other aspects, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of a compound of any of the formulae herein (e.g., formulae I-IV), such that said subject is treated for said disorder. Identifying a subject in need of such treatment can be in the judgment of a subject or a health care professional and can be subjective (e.g. opinion) or objective (e.g. measurable by a test or diagnostic method).

In certain embodiments, the invention provides a method as described above, wherein the compound of the formulae herein (e.g., formulae I-IV) is a largazole derivative.

In certain embodiments, the invention provides a method of treating a disorder, wherein the disorder is cancer (e.g., breast, colon) or solid tumor.

In certain embodiments, the subject is a mammal, preferably a primate or human.

In another embodiment, the invention provides a method as described above, wherein the effective amount of the compound of the formulae herein (e.g., formulae I-IV) ranges from about 0.005 µg/kg to about 200 mg/kg. In certain embodiments, the effective amount of the compound of the formulae herein (e.g., formulae I-IV) ranges from about 0.1 mg/kg to about 200 mg/kg. In a further embodiment, the effective amount of compound of the formulae herein (e.g., formulae I-IV) ranges from about 10 mg/kg to 100 mg/kg.

In other embodiments, the invention provides a method as described above wherein the effective amount of the compound of the formulae herein (e.g., formulae I-IV) ranges from about 1.0 pM to about 500 nM. In certain embodiments, the effective amount ranges from about 10.0 pM to about 1000 pM. In another embodiment, the effective amount ranges from about 1.0 nM to about 10 nM.

In another embodiment, the invention provides a method as described above, wherein the compound of the formulae herein (e.g., formulae I-IV) is administered intravenously, intramuscularly, subcutaneously, intracerebroventricularly, orally or topically.

In another embodiment, the invention provides a method as described herein wherein the compound of the formulae herein (e.g., formulae I-IV) demonstrates selectivity (e.g., at least 2-fold, at least 5-fold, at least 10-fold, at least X-fold where X is any number between 1 and 20 inclusive) in cell growth activity (e.g., in transformed/nontransformed, MDA-MB-231/NMuMG, U2OS/NIH3T3 cells). In another aspect, the compound of the formulae herein (e.g., formulae I-IV) demonstrates selectivity in modulating cell growth activity (e.g., at least 2-fold, at least 5-fold, at least 10-fold, at least X-fold where X is any number between 1 and 20 inclusive) relative to another standard anticancer therapy (e.g., paclitaxel, actinomycin D, doxorubicin).

In other embodiments, the invention provides a method as described above, wherein the compound of the formulae herein (e.g., formulae I-IV) is administered alone or in combination with one or more other therapeutics. In a further embodiment, the additional therapeutic agent is an anti-cancer agent, chemotherapeutic agent, an anti-angiogenesis agent, cytotoxic agent, or an anti-proliferation agent. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). (See, generally, The Merck Manual of Diagnosis and Therapy, 15th Ed., pp. 1206-1228, Berkow et al., eds., Rahay, N.J., 1987).

Another object of the present invention is the use of a compound as described herein (e.g., of any formulae herein) in the manufacture of a medicament for use in the treatment of a cell proliferation disorder or disease. Another object of the present invention is the use of a compound as described herein (e.g., of any formulae herein) for use in the treatment of a cell proliferation disorder or disease.

Pharmaceutical Compositions

In one aspect, the invention provides a pharmaceutical composition comprising the compound of the formulae herein (e.g., formulae I-IV) and a pharmaceutically acceptable carrier.

In one embodiment, the invention provides a pharmaceutical composition wherein the compound of the formulae herein (e.g., formulae I-IV) is a largazole derivative, and a pharmaceutically acceptable carrier.

In another embodiment, the invention provides a pharmaceutical composition further comprising an additional therapeutic agent. In a further embodiment, the additional therapeutic agent is an anti-cancer agent, chemotherapeutic agent, an anti-angiogenesis agent, cytotoxic agent, or an anti-proliferation agent.

In one aspect, the invention provides a kit comprising an effective amount of a compound of the formulae herein (e.g., formulae I-IV), in unit dosage form, together with instructions for administering the compound to a subject suffering from or susceptible to a HDAC mediated disease or disorder, including memory loss, inducing neurogenesis, enhancing memory retention, enhancing memory formation, increasing synaptic potential or transmission, or increasing long term potentiation (LTP), etc.

In one aspect, the invention provides a kit comprising an effective amount of a compound of the formulae herein (e.g., formulae I-IV), in unit dosage form, together with instructions for administering the compound to a subject suffering from or susceptible to a cell proliferation disease or disorder, including cancer, solid tumor, angiogenesis, etc.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, and the nature of concurrent therapy. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Definitions of variables in the structures in the schemes herein are to be taken as commensurate with those of corresponding positions in the formulae delineated herein.

EXAMPLES

The present invention will now be demonstrated using specific examples that are not to be construed as limiting.

General Experimental Procedures

Unless otherwise stated, all reagents were purchased from Sigma-Aldrich, Acros, Chem-Impex, or Fischer and were used without further purification. All solvents were ACS grade or better and used without further purification except THF which was freshly distilled each time before use. Thin layer chromatography was performed with glass backed silica gel (60 Å) plates purchased from Whatman and visualized with 254 nm UV light. All chromatographic purifications were conducted via flash chromatography using ultra-pure silica gel (230-400 mesh, 60 Å) purchased from Silicycle as the stationary phase unless otherwise noted. All spectra were recorded in CDCl$_3$ unless otherwise noted, using a 400 MHz or 500 MHz Varian NMR spectrometer.

Example 1: Preparation of Representative Compounds

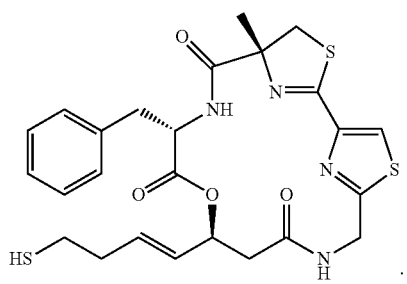

-continued

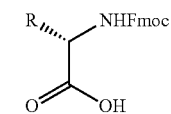

51a, R = CH$_2$Ph
51b, R = CH$_2$-p-OtBu-Ph a →

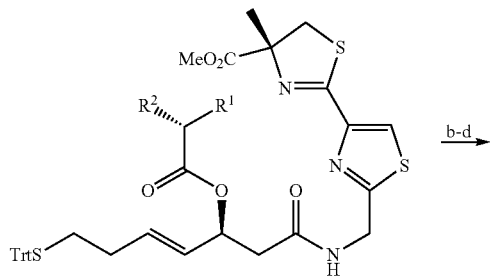

53a, R$^1$ = NHFmoc
R$^2$ = CH$_2$Ph
53b, R$^1$ = NHFmoc
R$^2$ = CH$_2$-p-OtBu-Ph b-d →

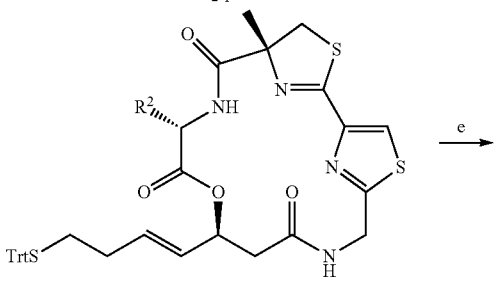

54a, R = CH$_2$Ph
54b, R = CH$_2$-p-OtBu-Ph e →

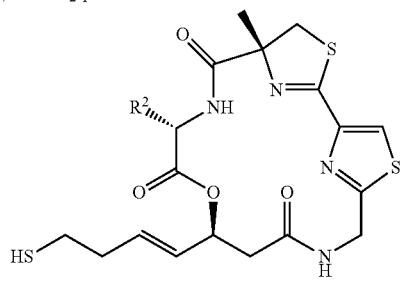

3, R = CH$_2$Ph
4, R = CH$_2$-p-OH-Ph

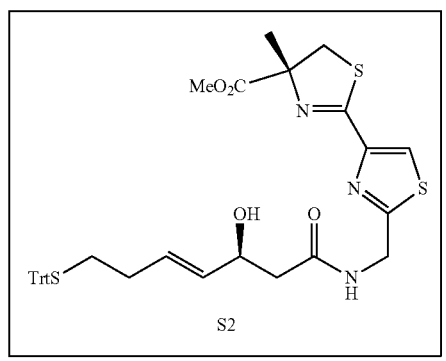

S2

Preparation of Compound 3

To a cooled (0° C.) solution of S1a (35.4 mg, 0.0915 mmol) in THF (5 mL) were added 2,4,6-trichlorobenzoyl chloride (15.3 μL, 0.0980 mmol) and Et$_3$N (14.6 μL, 0.105 mmol). After stirring for 2 h at 0° C., S2 (43.9 mg, 0.0653 mmol) (which was prepared as described in Numajiri, Y.; Takahashi, T.; Takagi, M.; Shin-Ya, K.; Doi, T. Synlett 2008, 2483), THF (3 mL) and DMAP (9.58 mg, 0.0784 mmol) were added at 0° C. After stirring for 1 h at 25° C., the reaction was quenched by the addition of saturated NH$_4$Cl solution and diluted with EtOAc. The layers were separated and the aqueous layer was extracted with EtOAc. The combined organic layers were dried over anhydrous Na$_2$SO$_4$ and concentrated in vacuo. The residue was purified by column chromatography (silica gel, EtOAc/hexanes/MeOH=10/10/1) to afford S3a (62.7 mg, 92%): $^1$H NMR (400 MHz, CDCl$_3$) δ 7.85 (s, 1H), 7.73 (d, J=7.6 Hz, 2H), 7.51 (dd, J=7.2, 3.2 Hz, 2H), 7.37 (dd, J=7.6, 7.6 Hz, 8H), 7.23-7.32 (m, 9H), 7.18 (dd, J=7.2, 7.2 Hz, 5H), 7.04 (d, J=6.4 Hz, 2H), 6.85 (dd, J=6.0, 6.0 Hz, 1H), 5.45-5.55 (m, 2H), 5.32 (dd, J=15.4, 7.2 Hz, 1H), 4.63 (d, J=5.6 Hz, 2H), 4.43 (dd, J=13.8, 6.4 Hz, 1H), 4.37 (dd, J=10.8, 7.2 Hz, 1H), 4.28 (dd, J=10.6, 6.8 Hz, 1H), 4.14 (dd, J=6.8, 6.8 Hz, 1H), 3.83 (d, J=11.2 Hz, 1H), 3.75 (s, 3H), 3.21 (d, J=11.0 Hz, 1H), 3.02 (dd, J=14.0, 6.8 Hz, 1H), 2.96 (dd, J=14.0, 6.8 Hz, 1H), 2.50 (d, J=6.0 Hz, 2H), 2.16 (dd, J=7.6, 7.6 Hz, 2H), 2.03 (br s, 2H), 1.61 (s, 3H).

To a cooled (0° C.) solution of S3a (45.1 mg, 0.0434 mmol) in THF/H$_2$O (4/1, 1.5 mL) was added 0.25 N LiOH (191 μL). After stirring for 3 h at 0° C., the reaction mixture was acidified by 0.25 N KHSO$_4$ until the pH of the solution reached 3. After dilution with EtOAc, the layers were separated and the aqueous layer was extracted with EtOAc. The combined organic layers were dried over anhydrous Na$_2$SO$_4$ and concentrated in vacuo. To a solution of the crude mixture in CH$_3$CN (5 mL) was added Et$_2$NH (0.5 mL) at 25° C. After stirring for 2 h at 25° C., the reaction mixture was concentrated in vacuo and washed with toluene. After removal of toluene in vacuo, to a solution of the crude mixture in CH$_2$Cl$_2$ (43.4 mL) were added HATU (33 mg, 0.0868 mmol) and i-Pr$_2$NEt (22.6 μL, 0.130 mmol) at 25° C. After stirring for 18 h at 25° C., the reaction mixture was concentrated in vacuo. The residue was diluted with H$_2$O and EtOAc. The layers were separated and the aqueous layer was extracted with EtOAc. The combined organic layers were dried over anhydrous Na$_2$SO$_4$ and concentrated in vacuo. The residue was purified by three iterations of column chromatography (silica gel, EtOAc/hexanes/MeOH=10/10/1, EtOAc/hexanes=1/1, EtOAc 100%) to afford S4a (5.8 mg, 17% for three steps): $^1$H NMR (400 MHz, CDCl$_3$) δ 7.63 (s, 1H), 7.16-7.34 (m, 15H), 6.86 (d, J=6.4 Hz, 2H), 6.77-6.79 (m, 3H), 6.04 (br s, 1H), 5.65-5.72 (m, 2H), 5.39 (dd, J=15.8, 6.8 Hz, 1H), 4.87 (m, 1H), 4.75 (dd, J=17.6, 7.2 Hz, 1H), 4.25 (dd, J=17.4, 4.0 Hz, 1H), 4.11 (d, J=11.6 Hz, 1H), 3.25 (d, J=11.2 Hz, 1H), 3.17 (dd, J=14.0, 3.6 Hz, 1H), 3.03 (dd, J=14.0, 5.6 Hz, 1H), 2.55-2.68 (m, 2H), 2.14 (dd, J=7.2, 7.2 Hz, 2H), 2.01 (dd, J=10.0, 10.0 Hz, 2H), 1.77 (s, 3H).

To a cooled (0° C.) solution of S4a (10 mg, 0.0127 mmol) in CH$_2$Cl$_2$ (3 mL) were added TFA (300 μL) and i-Pr$_3$SiH (5 μL, 0.0254 mmol). After stirring for 2 h at 25° C., the reaction mixture was concentrated in vacuo. The residue was purified by column chromatography (silica gel, EtOAc/hexanes/MeOH=15/15/1) to afford 3 (4.7 mg, 68%): $^1$H NMR (500 MHz, CDCl$_3$) δ 7.67 (s, 1H), 7.32 (d, J=7.5 Hz, 1H), 6.89 (d, J=7.0 Hz, 2H), 6.85 (dd, J=7.5, 7.5 Hz, 1H), 6.79 (d, J=7.5, 7.5 Hz, 2H), 5.93 (dd, J=4.5, 4.5 Hz, 1H), 5.83 (ddd, J=15.0, 7.5, 7.5 Hz, 1H), 5.75 (br s, 1H), 5.57 (dd, J=15.5, 5.5 Hz, 1H), 4.92-4.96 (m, 1H), 4.73 (dd, J=17.5, 6.5 Hz, 1H), 4.44 (dd, J=17.5, 4.0 Hz, 1H), 4.14 (d, J=11.5 Hz, 1H), 3.28 (d, J=11.5 Hz, 1H), 3.21 (dd, J=13.5, 3.0 Hz, 1H), 3.07 (dd, J=13.5, 6.0 Hz, 1H), 2.68 (dd, J=16.0, 7.0 Hz, 1H), 2.61 (dd, J=16.0, 3.0, 1H), 2.52 (ddd, J=7.5, 7.5, 7.5, 2H), 2.31-2.36 (m, 2H), 1.82 (s, 3H), 1.44 (dd, J=7.5, 7.5 Hz, 1H).

Preparation of Compound 4

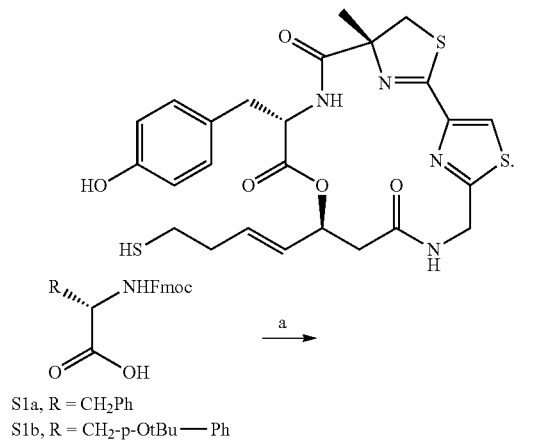

S1a, R = CH2Ph
S1b, R = CH2-p-OtBu—Ph

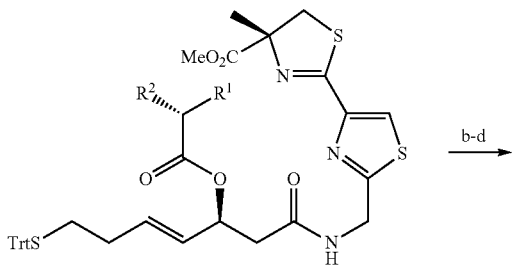

S3a, R¹ = NHFmoc
    R² = CH2Ph
S3b, R¹ = NHFmoc
    R² = CH2-p-OtBu—Ph

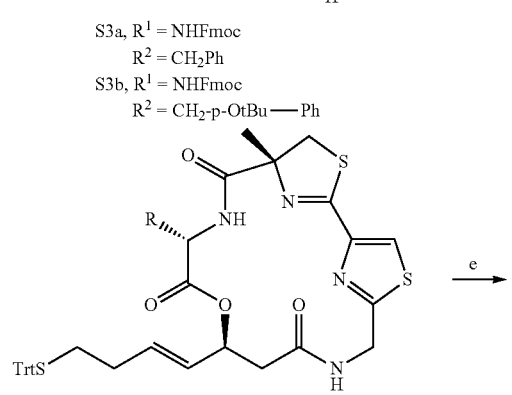

S4a, R = CH2Ph
S4b, R = CH2-p-OtBu—Ph

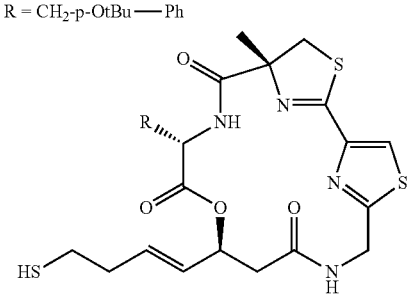

3, R = CH2Ph
4, R = CH2-p-OH—Ph

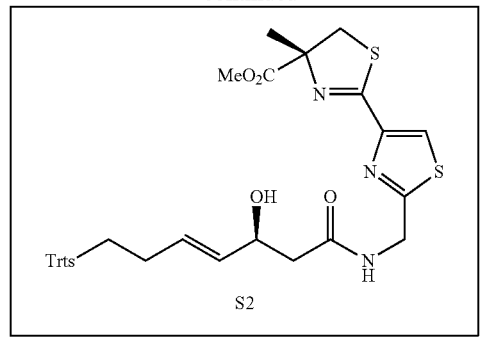

S2

To a cooled (0° C.) solution of S1b (103 mg, 0.225 mmol) in THF (5 mL) were added 2,4,6-trichlorobenzoyl chloride (37.7 μL, 0.241 mmol) and Et3N (35.8 μL, 0.257 mmol). After stirring for 2 h at 0° C., S2 (108 mg, 0.161 mmol) (which was prepared as described in Numajiri, Y.; Takahashi, T.; Takagi, M.; Shin-Ya, K.; Doi, T. Synlett 2008, 2483) in THF (3 mL) and DMAP (23.6 mg, 0.193 mmol) were added at 0° C. After stirring for 1 h at 25° C., the reaction was quenched by the addition of saturated NH4Cl solution and diluted with EtOAc. The layers were separated and the aqueous layer was extracted with EtOAc. The combined organic layers were dried over anhydrous Na2SO4 and concentrated in vacuo. The residue was purified by column chromatography (silica gel, EtOAc/hexanes/MeOH=10/10/1) to afford S3b (139 mg, 78%): $^1$H NMR (400 MHz, CDCl3) δ 7.85 (s, 1H), 7.73 (d, J=7.6 Hz, 2H), 7.51 (d, J=7.2 Hz, 2H), 7.18-7.42 (m, 19H), 6.94 (d, J=8.4 Hz, 2H), 6.84 (d, J=8.4 Hz, 2H), 5.52-5.63 (m, 2H), 5.32 (dd, J=16.2, 7.6 Hz, 1H), 4.64 (d, J=6.4 Hz, 2H), 4.41 (dd, J=14.0, 6.4 Hz, 1H), 4.15-4.43 (m, 4H), 3.82 (d, J=11.6 Hz, 1H), 3.75 (s, 3H), 3.21 (d, J=11.6 Hz, 1H), 3.00 (dd, J=14.0, 6.4 Hz, 1H), 2.89 (dd, J=14.0, 6.4 Hz, 1H), 2.51 (d, J=6.0 Hz, 2H), 2.18 (dd, J=7.2, 7.2 Hz, 2H), 2.05 (m, 2H), 1.60 (s, 3H), 1.29 (s, 9H).

To a cooled (0° C.) solution of S3b (81.5 mg, 0.0733 mmol) in THF/H2O (4/1, 2.5 mL) was added 0.25 N LiOH (322 μL). After stirring for 3 h at 0° C., the reaction mixture was acidified by 0.25 N KHSO4 until the pH of the solution reached 3. After dilution with EtOAc, the layers were separated and the aqueous layer was extracted with EtOAc. The combined organic layers were dried over anhydrous Na2SO4 and concentrated in vacuo. To a solution of the crude mixture in CH3CN (5 mL) was added Et2NH (0.5 mL) at 25° C. After stirring for 2 h at 25° C., the reaction mixture was concentrated in vacuo and washed with toluene. After removal of toluene in vacuo, to a solution of the crude mixture in CH2Cl2 (73.3 mL) were added HATU (55.9 mg, 0.147 mmol) and i-Pr2NEt (38.3 μL, 0.220 mmol) at 25° C. After stirring for 18 h at 25° C., the reaction mixture was concentrated in vacuo. The residue was diluted with H2O and EtOAc. The layers were separated and the aqueous layer was extracted with EtOAc. The combined organic layers were dried over anhydrous Na2SO4 and concentrated in vacuo. The residue was purified by three iterations of column chromatography (silica gel, EtOAc/hexanes/MeOH=10/10/1, EtOAc/hexanes=1/1, EtOAc 100%) to afford S4b (7.8 mg, 13% for three steps): $^1$H NMR (400 MHz, CDCl3) δ 7.66 (s, 1H), 7.15-7.34 (m, 15H), 6.73 (d, J=8.4 Hz, 2H), 6.33 (d, J=8.4 Hz, 2H), 5.99 (br s, 1H), 5.62-5.70 (m, 2H), 5.44 (dd, J=15.4, 6.8 Hz, 1H), 4.86 (m, 1H), 4.71 (dd, J=17.6, 6.4 Hz, 1H), 4.37 (dd, J=17.4, 4.4 Hz, 1H), 4.09 (d, J=11.2 Hz, 1H), 3.24 (d, J=11.6 Hz, 1H), 3.10 (m, 1H), 2.99 (dd, J=13.6, 5.2 Hz, 1H), 2.60 (dd, J=16.0, 6.4 Hz, 1H), 2.53 (dd, J=16.2, 2.8 Hz, 1H), 2.14 (dd, J=7.2, 7.2 Hz, 2H), 2.00 (ddd, J=6.8, 6.8, 6.8 Hz, 2H), 1.76 (s, 3H), 1.20 (s, 9H).

To a cooled (0° C.) solution of S4b (6 mg, 0.00747 mmol) in CH$_2$Cl$_2$ (3 mL) were added TFA (300 μL) and i-Pr$_3$SiH (3 μL, 0.0149 mmol). After stirring for 2 h at 25° C., the reaction mixture was concentrated in vacuo. The residue was purified by column chromatography (silica gel, EtOAc/hexanes/MeOH=15/15/1) to afford 3 (2.5 mg, 60%): $^1$H NMR (500 MHz, CD$_3$OD) δ 7.98 (s, 1H). 7.29 (d, J=8.0 Hz, 1H), 6.64 (d, J=8.5 Hz, 2H), 6.27 (d, J=8.5 Hz, 2H), 5.85 (ddd, J=14.5, 7.0, 7.0 Hz, 1H), 5.75 (dd, J=4.5, 4.5 Hz 1H), 6.12 (dd, J=15.5, 7.0 Hz, 1H), 5.02 (d, J=17.5 Hz, 1H), 4.72-4.76 (m, 1H), 4.34 (d, J=17.5 Hz, 1H), 3.93 (d, J=11.5 Hz, 1H), 3.35 (d, J=11.5 Hz, 1H), 3.08 (dd, J=14.0, 4.0 Hz, 1H), 2.94 (dd, J=16.0, 10.0 Hz, 1H), 2.90 (dd, J=14.0, 5.5 Hz, 1H), 2.65 (dd, J=16.5, 2.5 Hz, 1H), 2.54 (dd, J=7.5, 7.5 Hz, 2H), 2.35 (ddd, J=7.5, 7.5, 7.5 Hz, 2H), 1.76 (s, 3H).

Preparation of Compound 5

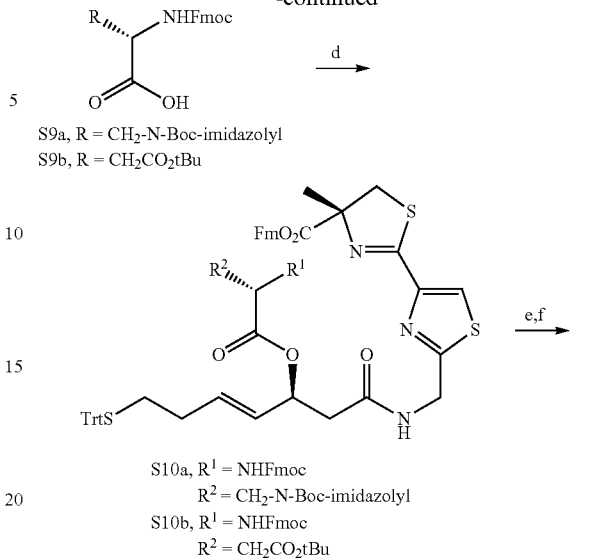

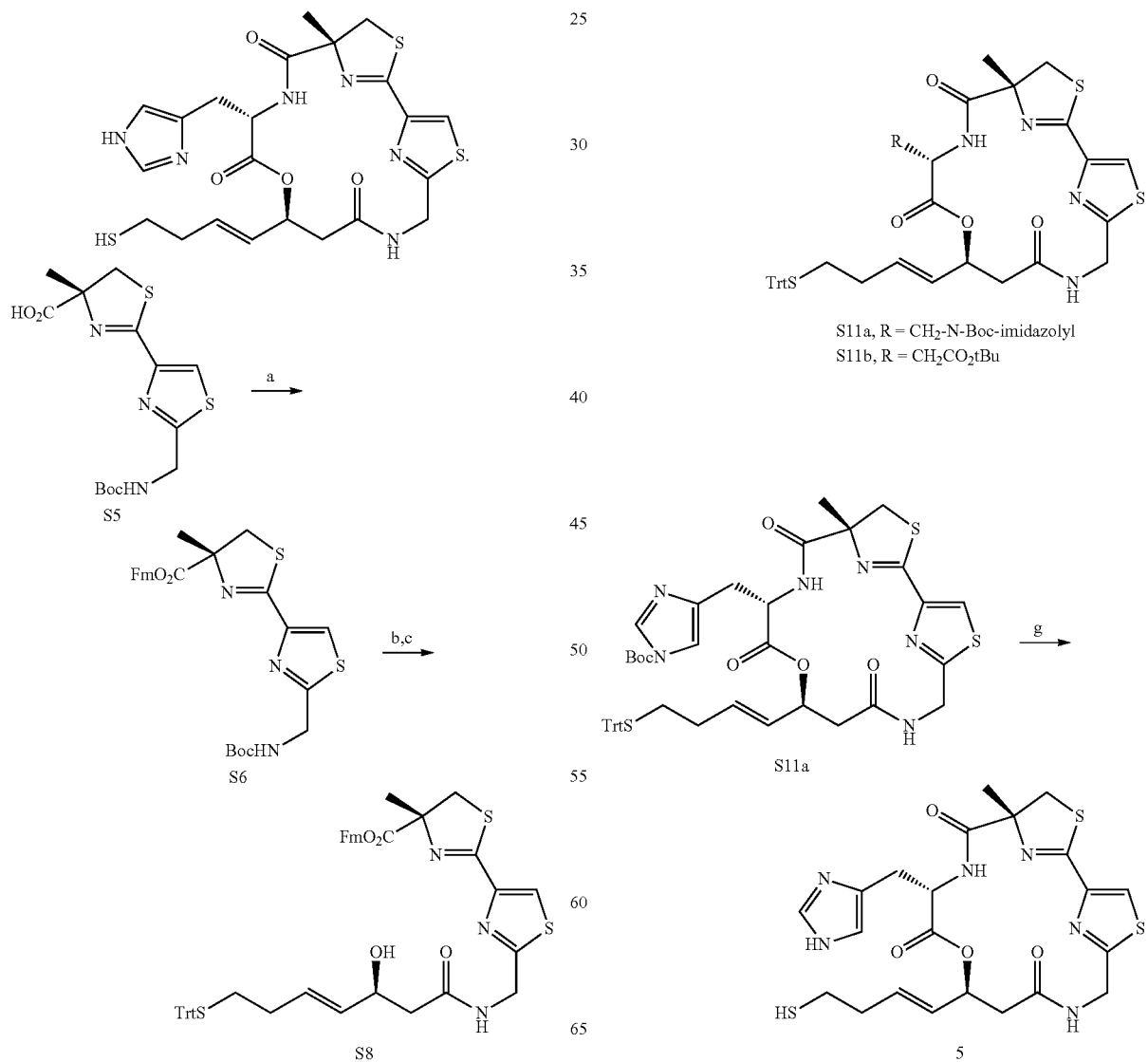

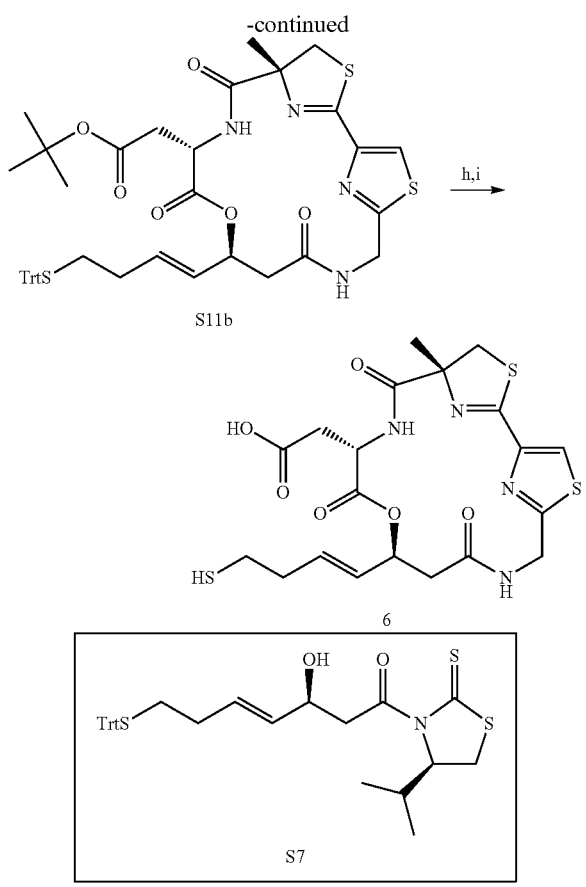

Hz, 2H), 7.43 (d, J=7.2 Hz, 2H), 7.17-7.40 (m, 19H), 6.84 (dd, J=5.6, 5.6 Hz, 1H), 5.56 (ddd, J=15.2, 5.6, 5.6 Hz, 1H), 5.42 (dd, J=15.6, 6.0 Hz, 1H), 4.75 (dd, J=6.0, 6.0 Hz, 2H), 4.51 (d, J=7.2 Hz, 2H), 4.44 (br s, 1H), 4.26 (dd, J=6.8, 6.8 Hz, 1H), 3.77 (d, J=11.6 Hz, 1H), 3.24 (d, J=11.6 Hz, 1H), 2.46 (dd, J=15.2, 3.6 Hz, 1H), 2.39 (dd, J=15.2, 8.4 Hz, 1H), 2.19 (dd, J=8.0, 8.0 Hz, 2H), 2.06 (dd, J=15.0, 6.8 Hz, 2H), 1.70 (s, 3H).

To a cooled (0° C.) solution of S9a (65.4 mg, 0.137 mmol) in THF (5 mL) were added 2,4,6-trichlorobenzoyl chloride (32.2 μL, 0.206 mmol) and Et$_3$N (33.6 μL, 0.241 mmol). After stirring for 2 h at 0° C., S8 (57.4 mg, 0.0687 mmol) in THF (3 mL) and DMAP (16.8 mg, 0.138 mmol) were added at 0° C. After stirring for 1 h at 25° C., the reaction was quenched by the addition of saturated NH$_4$Cl solution and diluted with EtOAc. The layers were separated and the aqueous layer was extracted with EtOAc. The combined organic layers were dried over anhydrous Na$_2$SO$_4$ and concentrated in vacuo. The residue was purified by column chromatography (silica gel, EtOAc/hexanes=1/1) to afford S10a (105 mg, 96%): $^1$H NMR (400 MHz, CDCl$_3$) δ 8.02 (s, 1H), 7.72 (dd, J=7.2, 7.2 Hz 4H), 7.60 (d, J=7.2 Hz, 2H), 7.53 (dd, J=7.2, 7.2 Hz, 2H), 7.34-7.40 (m, 10H), 7.23-7.29 (m, 11H), 7.13-7.21 (m, 4H), 6.15 (d, J=7.2 Hz, 1H), 5.62 (ddd, J=17.6, 7.6, 7.6 Hz, 1H), 5.49-5.52 (m, 2H), 4.69 (d, J=6.4 Hz, 2H), 4.47 (dd, J=7.2, 2.4 Hz, 4H), 4.30 (d, J=7.2 Hz, 1H), 4.23 (dd, J=7.2, 7.2 Hz, 1H), 4.16 (dd, J=15.4, 6.8 Hz, 1H), 3.75 (d, J=11.6 Hz, 1H), 3.19 (d, J=11.6 Hz, 1H), 2.99 (dd, J=4.4, 4.4 Hz, 2H), 2.61 (br s, 2H), 2.19 (dd, J=6.4, 6.4 Hz, 2H), 2.05 (br s, 2H), 1.63 (s, 3H), 1.58 (s, 9H).

To a solution of S10a (75 mg, 0.0579 mmol) in CH$_3$CN (10 mL) was added Et$_2$NH (5 mL) at 25° C. After stirring for 1 h at 25° C., the reaction mixture was concentrated in vacuo and washed with toluene. After removal of toluene in vacuo, to a solution of the crude mixture in CH$_2$Cl$_2$ (65.8 mL) were added HATU (45.2 mg, 0.119 mmol) and i-Pr$_2$NEt (30.3 μL, 0.174 mmol) at 25° C. After stirring for 18 h at 25° C., the reaction mixture was concentrated in vacuo. The residue was diluted with H$_2$O and EtOAc. The layers were separated and the aqueous layer was extracted with EtOAc. The combined organic layers were dried over anhydrous Na$_2$SO$_4$ and concentrated in vacuo. The residue was purified by column chromatography (silica gel, EtOAc/hexanes/MeOH=30/30/1) to afford S11a (14.6 mg, 27% for two steps): $^1$H NMR (400 MHz, CDCl$_3$): δ 7.62 (s, 1H), 7.16-7.38 (m, 16H), 6.87 (s, 1H), 6.54 (br s, 1H), 5.66-5.71 (m, 2H), 5.42 (dd, J=15.6, 7.2 Hz, 1H), 4.96 (dd, J=17.6, 4.0 Hz, 1H), 4.80 (ddd, J=7.6, 4.8, 4.8 Hz, 1H), 4.32 (dd, J=12.4, 3.2 Hz, 1H), 4.10 (d, J=11.2 Hz, 1H), 3.24 (d, J=11.2 Hz, 1H), 3.07 (d, J=4.0 Hz, 2H), 2.77 (dd, J=16.0, 2.7 Hz, 1H), 2.68 (dd, J=16.4, 8.0 Hz, 1H), 2.17 (dd, J=7.2, 7.2 Hz, 2H), 2.04 (m, 2H), 1.79 (s, 3H), 1.57 (s, 9H).

To a cooled (0° C.) solution of S11a (8.5 mg, 0.00969 mmol) in CH$_2$Cl$_2$ (3 mL) were added TFA (300 μL) and i-Pr$_3$SiH (7 μL, 0.0254 mmol). After stirring for 1 h at 25° C., the reaction mixture was concentrated in vacuo. The residue was purified by column chromatography (silica gel, CHCl$_3$/MeOH=10/1) to afford 5 (2.5 mg, 48%): $^1$H NMR (500 MHz, CD$_3$OD) δ 7.99 (s, 1H), 7.28 (d, J=7.5 Hz, 1H), 7.25 (s, 1H), 6.53 (s, 1H), 5.86 (ddd, J=22.5, 7.0, 7.0 Hz, 1H), 5.83 (dd, J=4.5, 4.5 Hz, 1H), 5.63 (dd, J=16.0, 7.0 Hz, 1H), 5.18 (d, J=17.5 Hz, 1H), 4.75-4.77 (m, 1H), 4.38 (d, J=17.5 Hz, 1H), 3.86 (d, J=11.5 Hz, 1H), 3.19 (dd, J=15.5, 6.0 Hz, 1H), 3.10 (dd, J=15.5, 4.0 Hz, 1H), 3.05 (dd, J=17.0, To a solution of S5 (468.7 mg, 1.31 mmol) (which was prepared as described in Bowers, A.; West, N.; Taunton, J.; Schreiber, S. L.; Bradner, J. E.; Williams, R. M. *J. Am. Chem. Soc.* 2008, 130, 11219) in CH$_2$Cl$_2$ (35 mL) were added 9-fluorenemethanol (386.6 mg, 1.97 mmol), EDCI (504.2 mg, 2.63 mmol), and DMAP (160.0 mg, 1.31 mmol) at 25° C. After stirring for 2 h at 25° C., the reaction mixture was concentrated in vacuo. The residue was purified by column chromatography (silica gel, EtOAc/hexanes=1/3) to afford S6 (441.7 mg, 63%): $^1$H NMR (400 MHz, CDCl$_3$) δ 7.98 (s, 1H), 7.74 (dd, J=7.6, 4.4 Hz, 2H), 7.63 (dd, J=7.2, 0.4 Hz, 2H), 7.38 (ddd, J=10.4, 7.2, 7.2 Hz, 2H), 7.24 (ddd, J=23.6, 7.6, 7.6 Hz, 2H), 5.47 (br s, 1H), 4.66 (d, J=6.0 Hz, 2H), 4.51 (d, J=7.6 Hz, 2H), 4.27 (dd, J=6.8, 6.8 Hz, 1H), 3.79 (d, J=11.2 Hz, 1H), 3.24 (d, J=11.6 Hz, 1H), 1.67 (s, 3H), 1.41 (s, 9H).

To a solution of S6 (603.9 mg, 1.13 mmol) in CH$_2$Cl$_2$ (32 mL) was added TFA (8 mL) at 25° C. After stirring for 1 h at 25° C., the reaction mixture was concentrated in vacuo and washed with Et$_2$O. To a solution of the crude mixture in CH$_2$Cl$_2$ (40 mL) were added S7 (478.6 mg, 0.852 mmol) (which was prepared as described in Yurek-George, A.; Habens, F.; Brimmell, M.; Packham, G.; Ganesan, A. *J. Am. Chem. Soc.* 2004, 126, 1030) in CH$_2$Cl$_2$ (5 mL) and DMAP (690.3 mg, 5.565 mmol) at 25° C. After stirring for 2 h at 25° C., the reaction was quenched by the addition of H$_2$O. The layers were separated and the aqueous layer was extracted with CH$_2$Cl$_2$. The combined organic layers were dried over anhydrous Na$_2$SO$_4$ and concentrated in vacuo. The residue was purified by column chromatography (silica gel, EtOAc/hexanes=1/1) to afford S8 (660.6 mg, 93% for two steps): $^1$H NMR (400 MHz, CDCl$_3$) δ 8.04 (s, 1H), 7.73 (dd, J=6.8, 6.8

11.0 Hz, 1H), 2.77 (dd, J=17.0, 2.5 Hz, 1H), 2.56 (dd, J=7.5, 7.5 Hz, 2H), 2.37 (ddd, J=6.0, 6.0, 6.0 Hz, 2H), 1.75 (s, 3H).
Preparation of Compound 6
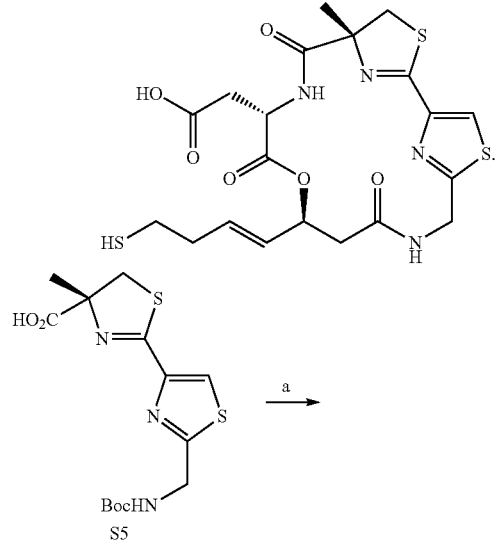
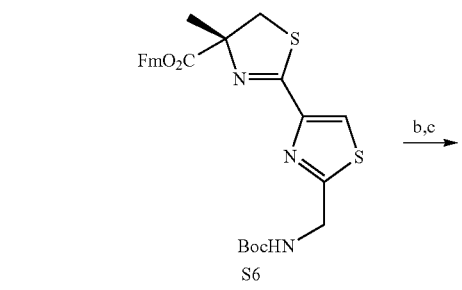
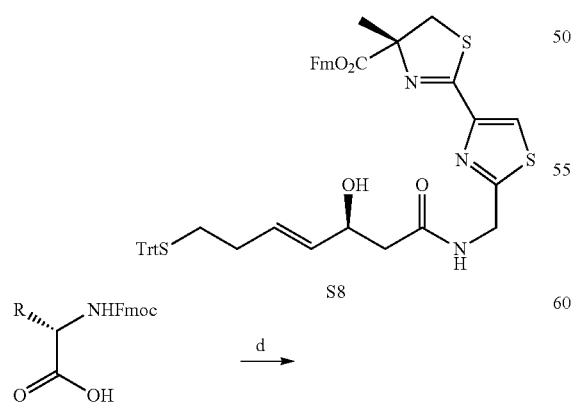
S9a, R = CH$_2$-N-Boc-imidazolyl
S9b, R = CH$_2$CO$_2$tBu
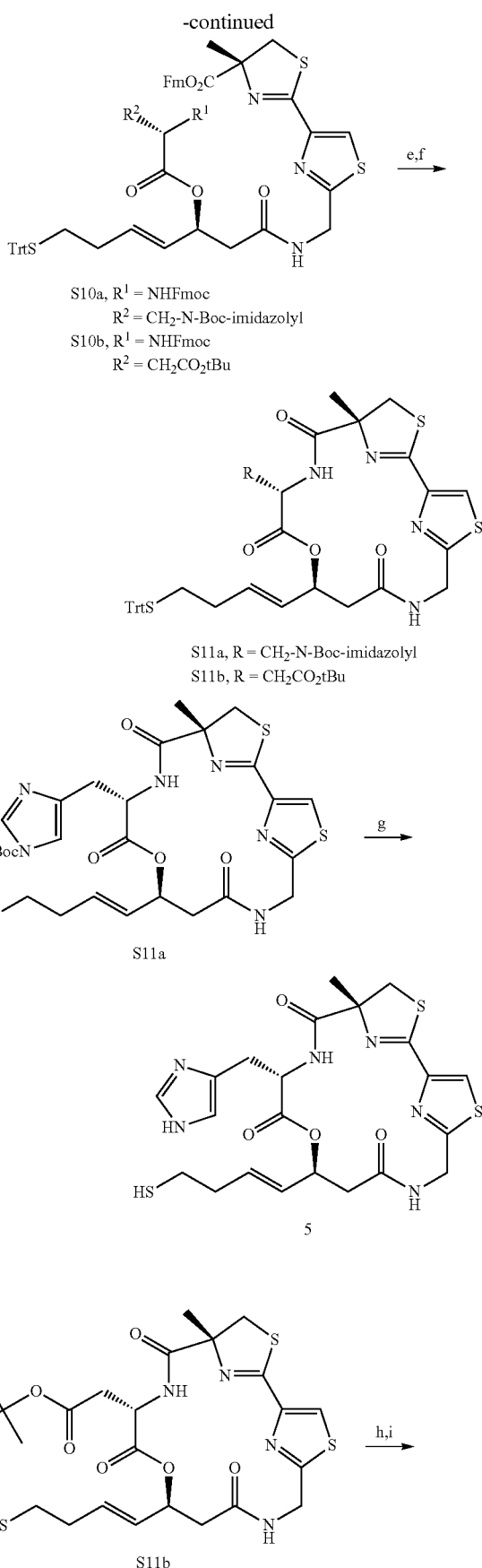
S10a, R$^1$ = NHFmoc
R$^2$ = CH$_2$-N-Boc-imidazolyl
S10b, R$^1$ = NHFmoc
R$^2$ = CH$_2$CO$_2$tBu
S11a, R = CH$_2$-N-Boc-imidazolyl
S11b, R = CH$_2$CO$_2$tBu
S11a
5
S11b -continued

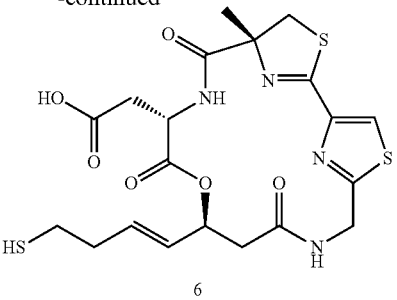

6

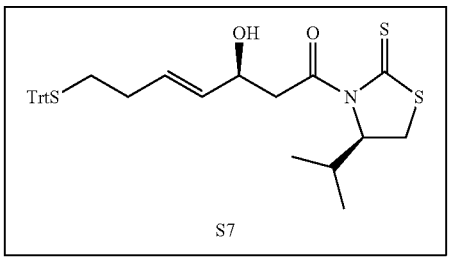

S7

To a solution of S5 (468.7 mg, 1.31 mmol) (which was prepared as described in Bowers, A.; West, N.; Taunton, J.; Schreiber, S. L.; Bradner, J. E.; Williams, R. M. *J. Am. Chem. Soc.* 2008, 130, 11219) in $CH_2Cl_2$ (35 mL) were added 9-fluorenemethanol (386.6 mg, 1.97 mmol), EDCI (504.2 mg, 2.63 mmol), and DMAP (160.0 mg, 1.31 mmol) at 25° C. After stirring for 2 h at 25° C., the reaction mixture was concentrated in vacuo. The residue was purified by column chromatography (silica gel, EtOAc/hexanes=1/3) to afford S6 (441.7 mg, 63%): $^1$H NMR (400 MHz, $CDCl_3$) δ 7.98 (s, 1H), 7.74 (dd, J=7.6, 4.4 Hz, 2H), 7.63 (dd, J=7.2, 0.4 Hz, 2H), 7.38 (ddd, J=10.4, 7.2, 7.2 Hz, 2H), 7.24 (ddd, J=23.6, 7.6, 7.6 Hz, 2H), 5.47 (br s, 1H), 4.66 (d, J=6.0 Hz, 2H), 4.51 (d, J=7.6 Hz, 2H), 4.27 (dd, J=6.8, 6.8 Hz, 1H), 3.79 (d, J=11.2 Hz, 1H), 3.24 (d, J=11.6 Hz, 1H), 1.67 (s, 3H), 1.41 (s, 9H).

To a solution of S6 (603.9 mg, 1.13 mmol) in $CH_2Cl_2$ (32 mL) was added TFA (8 mL) at 25° C. After stirring for 1 h at 25° C., the reaction mixture was concentrated in vacuo and washed with $Et_2O$. To a solution of the crude mixture in $CH_2Cl_2$ (40 mL) were added S7 (478.6 mg, 0.852 mmol) (which was prepared as described in Yurek-George, A.; Habens, F.; Brimmell, M.; Packham, G.; Ganesan, A. *J. Am. Chem. Soc.* 2004, 126, 1030) in $CH_2Cl_2$ (5 mL) and DMAP (690.3 mg, 5.565 mmol) at 25° C. After stirring for 2 h at 25° C., the reaction was quenched by the addition of $H_2O$. The layers were separated and the aqueous layer was extracted with $CH_2Cl_2$. The combined organic layers were dried over anhydrous $Na_2SO_4$ and concentrated in vacuo. The residue was purified by column chromatography (silica gel, EtOAc/hexanes=1/1) to afford S8 (660.6 mg, 93% for two steps): $^1$H NMR (400 MHz, $CDCl_3$) δ 8.04 (s, 1H), 7.73 (dd, J=6.8, 6.8 Hz, 2H), 7.43 (d, J=7.2 Hz, 2H), 7.17-7.40 (m, 19H), 6.84 (dd, J=5.6, 5.6 Hz, 1H), 5.56 (ddd, J=15.2, 5.6, 5.6 Hz, 1H), 5.42 (dd, J=15.6, 6.0 Hz, 1H), 4.75 (dd, J=6.0, 6.0 Hz, 2H), 4.51 (d, J=7.2 Hz, 2H), 4.44 (br s, 1H), 4.26 (dd, J=6.8, 6.8 Hz, 1H), 3.77 (d, J=11.6 Hz, 1H), 3.24 (d, J=11.6 Hz, 1H), 2.46 (dd, J=15.2, 3.6 Hz, 1H), 2.39 (dd, J=15.2, 8.4 Hz, 1H), 2.19 (dd, J=8.0, 8.0 Hz, 2H), 2.06 (dd, J=15.0, 6.8 Hz, 2H), 1.70 (s, 3H).

To a cooled (0° C.) solution of S9b (52.0 mg, 0.126 mmol) in THF (10 mL) were added 2,4,6-trichlorobenzoyl chloride (21 μL, 0.134 mmol) and $Et_3N$ (20 μL, 0.142 mmol). After stirring for 2 h at 0° C., S8 (75 mg, 0.089 mmol) in THF (4 mL) and DMAP (13 mg, 0.197 mmol) were added at 0° C. After stirring for 1 h at 25° C., the reaction was quenched by the addition of saturated $NH_4Cl$ solution and diluted with EtOAc. The layers were separated and the aqueous layer was extracted with EtOAc. The combined organic layers were dried over anhydrous $Na_2SO_4$ and concentrated in vacuo. The residue was purified by column chromatography (silica gel, EtOAc/hexanes=1/1) to afford S10b (82.7 mg, 93%): $^1$H NMR (500 MHz, $CDCl_3$) δ 7.91 (s, 1H), 7.74 (dd, J=7.0, 7.0 Hz, 4H), 7.73 (d, J=7.5 Hz, 2H), 7.55 (dd, J=8.0, 8.0 Hz, 2H), 7.35-7.41 (m, 10H), 7.26-7.30 (m, 10H), 7.20 (dd, J=7.5, 7.5 Hz, 3H), 6.86 (br s, 1H), 5.84 (d, J=8.5 Hz, 1H), 5.66 (ddd, J=15.0, 7.0, 7.0 Hz, 1H), 5.59 (dd, J=12.8, 6.5 Hz, 1H), 5.44 (dd, J=15.3, 6.5 Hz, 1H), 4.71 (d, J=6.0 Hz, 2H), 4.56 (m, 1H), 4.50 (dd, J=6.5, 4.0 Hz, 2H), 4.41 (dd, J=10.0, 7.5 Hz, 1H), 4.35 (dd, J=10.0, 7.5 Hz, 1H), 4.25 (dd, J=7.0, 7.0 Hz, 1H), 4.20 (dd, J=7.0, 7.0 Hz, 1H), 3.78 (d, J=11.5 Hz, 1H), 3.22 (d, J=11.5 Hz, 1H), 2.88 (dd, J=17.0, 5.0 Hz, 1H), 2.75 (dd, J=17.0, 5.0 Hz, 1H), 2.59 (d, J=5.5 Hz, 2H), 2.20 (dd, J=6.5, 6.5 Hz, 2H), 2.05 (m, 2H), 1.65 (s, 3H), 1.40 (s, 9H).

To a solution of S10b (100 mg, 0.081 mmol) in $CH_3CN$ (10 mL) was added $Et_2NH$ (2 mL) at 25° C. After stirring for 1 h at 25° C., the reaction mixture was concentrated in vacuo and washed with toluene. After removal of toluene in vacuo, to a solution of the crude mixture in $CH_2Cl_2$ (100 mL) were added HATU (61.5 mg, 0.162 mmol) and i-$Pr_2NEt$ (42.3 μL, 0.243 mmol) at 25° C. After stirring for 18 h at 25° C., the reaction mixture was concentrated in vacuo. The residue was diluted with $H_2O$ and EtOAc. The layers were separated and the aqueous layer was extracted with EtOAc. The combined organic layers were dried over anhydrous $Na_2SO_4$ and concentrated in vacuo. The residue was purified by column chromatography (silica gel, EtOAc/hexanes/MeOH=30/30/1) to afford S11b (41 mg, 62% for two steps): $^1$H NMR (400 MHz, $CD_3OD$) δ 8.02 (s, 1H), 7.56 (d, J=6.8, 1H), 7.34 (m, 6H), 7.28 (m, 6H), 7.20 (m, 3H), 5.66-5.73 (m, 2H), 5.47 (dd, J=15.4, 6.4 Hz, 1H), 5.51 (ddd, J=17.6, 4.4, 4.4 Hz, 1H), 4.56-4.60 (m, 1H), 4.45 (dd, J=17.2, 3.6 Hz, 1H), 3.87 (d, J=11.6 Hz, 1H), 3.40 (d, J=12.0 Hz, 1H), 2.96 (dd, J=16.4, 10.4 Hz, 1H), 2.75 (dd, J=13.6, 3.6 Hz, 1H), 2.68 (dd, J=16.8, 5.2 Hz, 1H), 2.17 (dd, J=7.2, 7.2 Hz, 2H), 2.04 (m, 2H), 1.77 (s, 3H), 1.20 (s, 9H).

To a cooled (0° C.) solution of S11b (10 mg, 0.0123 mmol) in $CH_2Cl_2$ (2 mL) were added TFA (200 μL) and i-$Pr_3SiH$ (5 μL, 0.0149 mmol). After stirring for 15 min at 0° C., the reaction mixture was concentrated in vacuo. The residue was purified by column chromatography (silica gel, EtOAc/hexanes/MeOH=10/10/1) to afford 6 (1.4 mg, 22% for two steps): $^1$H NMR (500 MHz, $CDCl_3$) δ 7.85 (d, J=7.5 Hz, 1H), 7.62 (s, 1H), 7.37 (br s, 1H), 5.91 (ddd, J=15.0, 7.0, 7.0 Hz, 1H), 5.75 (dd, J=15.0, 7.0 Hz, 1H), 5.68 (dd, J=4.5, 4.5 Hz, 1H), 5.04 (dd, J=17.0, 6.5 Hz, 1H), 4.66-4.69 (m, 1H), 4.63 (dd, J=17.0, 3.5 Hz, 1H), 4.01 (d, J=11.5 Hz, 1H), 3.27 (d, J=11.5 Hz, 1H), 2.97 (dd, J=17.5, 3.0 Hz, 1H), 2.91 (dd, J=15.0, 2.5 Hz, 1H), 2.80 (dd, J=17.5, 4.0 Hz, 1H), 2.69 (dd, J=15.0, 6.0 Hz, 1H), 2.54 (ddd, J=7.0, 7.0, 7.0 Hz, 2H), 2.38 (ddd, J=7.0, 7.0, 7.0 Hz, 2H), 1.84 (s, 3H), 1.54 (dd, J=8.0 Hz, 1H), 1.10 (s, 9H).

Preparation of Compound 9

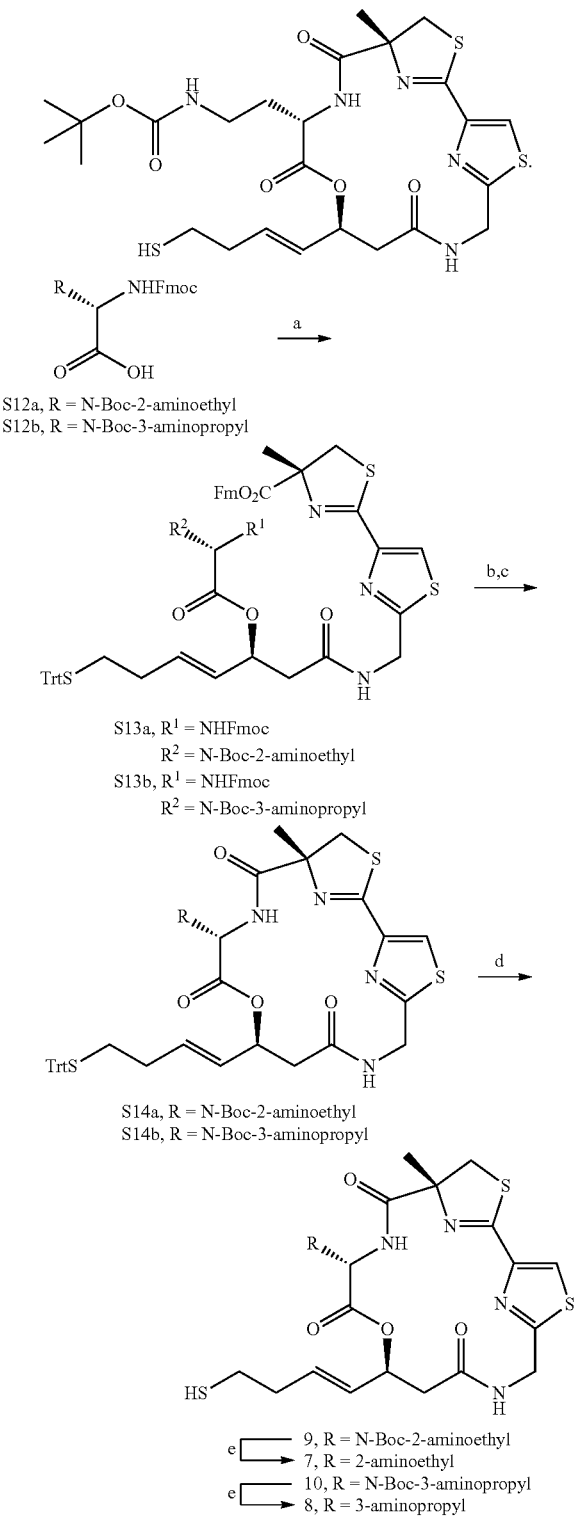

S12a, R = N-Boc-2-aminoethyl
S12b, R = N-Boc-3-aminopropyl

S13a, R¹ = NHFmoc
R² = N-Boc-2-aminoethyl
S13b, R¹ = NHFmoc
R² = N-Boc-3-aminopropyl S14a, R = N-Boc-2-aminoethyl
S14b, R = N-Boc-3-aminopropyl 9, R = N-Boc-2-aminoethyl
7, R = 2-aminoethyl
10, R = N-Boc-3-aminopropyl
8, R = 3-aminopropyl To a cooled (0° C.) solution of S12a (105.7 mg, 0.240 mmol) in THF (10 mL) were added 2,4,6-trichlorobenzoyl chloride (56.2 μL, 0.360 mmol) and Et₃N (58.5 μL, 0.420 mmol). After stirring for 2 h at 0° C., S8 (100.3 mg, 0.120 mmol) in THF (4 mL) and DMAP (29.3 mg, 0.240 mmol) were added at 0° C. After stirring for 1 h at 25° C., the reaction was quenched by the addition of saturated NH₄Cl solution and diluted with EtOAc. The layers were separated and the aqueous layer was extracted with EtOAc. The combined organic layers were dried over anhydrous Na₂SO₄ and concentrated in vacuo. The residue was purified by column chromatography (silica gel, EtOAc/hexanes=1/1) to afford S13a (146.4 mg, 91%): ¹H NMR (400 MHz, CDCl₃) δ 7.84 (s, 1H), 7.73 (d, J=7.2 Hz, 4H), 7.56 (d, J=7.2 Hz, 4H), 7.18-7.38 (m, 23H), 6.99 (br s, 1H), 5.60 (s, 1H), 5.58-5.68 (m, 2H), 5.42 (dd, J=14.8, 6.8 Hz, 1H), 4.65 (dd, J=5.6, 5.6 Hz, 2H), 4.48 (d, J=6.8 Hz, 2H), 4.16-4.37 (m, 5H), 3.67 (d, J=11.2 Hz, 1H), 3.18 (d, J=11.2 Hz, 1H), 2.85 (br s, 2H), 2.59 (dd, J=14.8, 8.0 Hz, 1H), 2.53 (dd, J=15.2, 4.8 Hz, 2H), 2.19 (dd, J=6.4, 6.4 Hz, 2H), 2.05 (d, J=6.8 Hz, 2H), 1.90 (br s, 2H), 1.58 (s, 3H), 1.42 (s, 9H).

To a solution of S13a (29.4 mg, 0.022 mmol) in CH₃CN (10 mL) was added Et₂NH (1 mL) at 25° C. After stirring for 2 h at 25° C., the reaction mixture was concentrated in vacuo and washed with toluene. After removal of toluene in vacuo, to a solution of the crude mixture in CH₂Cl₂ (25.0 mL) were added HATU (16.7 mg, 0.044 mmol) and i-Pr₂NEt (11.5 μL, 0.066 mmol) at 25° C. After stirring for 36 h at 25° C., the reaction mixture was concentrated in vacuo. The residue was diluted with H₂O and EtOAc. The layers were separated and the aqueous layer was extracted with EtOAc. The combined organic layers were dried over anhydrous Na₂SO₄ and concentrated in vacuo. The residue was purified by column chromatography (silica gel, EtOAc/hexanes/MeOH=30/30/1) to afford S14a (3.3 mg, 18% for two steps): ¹H NMR (400 MHz, CD₃OD) δ 8.11 (s, 1H), 7.38 (d, J=7.2 Hz, 6H), 7.28 (dd, J=7.2, 7.2 Hz, 6H), 7.21 (dd, J=8.4, 8.4 Hz, 3H), 6.56 (br s, 1H), 5.73 (ddd, J=15.2, 6.8, 6.8 Hz, 1H), 5.47-5.56 (m, 2H), 5.04 (d, J=17.6 Hz, 1H), 4.52 (dd, J=5.6, 5.6 Hz, 1H), 4.35 (d, J=17.6 Hz, 1H), 3.67 (d, J=11.6 Hz, 1H), 3.37 (d, J=11.6 Hz, 1H), 3.00 (dd, J=16.4, 1.4 Hz, 1H), 2.85 (m, 2H), 2.72 (dd, J=17.2, 2.8 Hz, 1H), 2.21 (dd, J=5.6, 5.6 Hz, 2H), 2.07 (dd, J=6.8, 6.8 Hz, 2H), 1.77 (s, 3H), 1.40 (s, 9H).

To a cooled (0° C.) solution of S14a (11.2 mg, 0.0131 mmol) in CH₂Cl₂ (2 mL) were added TFA (200 μL) and i-Pr₃SiH (5 μL, 0.0262 mmol). After stirring for 15 min at 0° C., the reaction mixture was concentrated in vacuo. The residue was purified by column chromatography (silica gel, EtOAc 100%) to afford 9 (4.3 mg, 54%): ¹H NMR (400 MHz, CD₃OD) δ 8.12 (s, 1H), 7.45 (d, J=8.0 Hz, 1H), 6.58 (br s, 1H), 5.83 (ddd, J=14.4, 6.8, 6.8 Hz, 1H), 5.61-5.67 (m, 2H), 5.06 (d, J=17.6 Hz, 1H), 4.54 (ddd, J=8.0, 5.2, 5.2 Hz, 1H), 4.41 (d, J=17.6 Hz, 1H), 3.97 (d, J=11.6 Hz, 1H), 3.38 (d, J=11.6 Hz, 1H), 3.07 (dd, J=10.4, 8.4 Hz, 1H), 2.77 (dd, J=18.0, 2.4 Hz, 1H), 2.55 (dd, J=7.2, 7.2 Hz, 2H), 2.36 (ddd, J=6.8, 6.8, 6.8 Hz, 2H), 1.89 (m, 2H), 1.79 (s, 3H), 1.41 (s, 9H).

Preparation of Compound 7

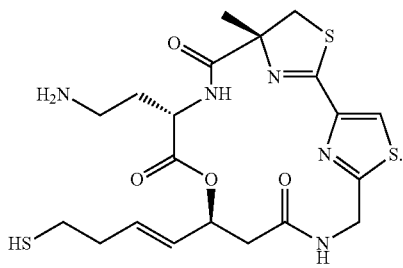 [SMILES: C[C@@]12CSC(=N1)c1csc(n1)CNC(=O)C[C@@H](/C=C/CCS)OC(=O)[C@H](CCN)NC2=O]

To a solution of 9 (4.0 mg, 0.0067 mmol) in CH$_2$Cl$_2$ (0.1 mL) was added TFA (10 μL). The reaction mixture was stirred for 1 h at 25° C. until there was no more starting material left (detected by MS). The reaction mixture was purged with N$_2$ and dried in vacuo to remove TFA and CH$_2$Cl$_2$. The crude mixture was purified by HPLC (Syringe-Hydro RP, 4 μm, flow rate 2.0 mL/min) eluting with of MeOH/H$_2$O (MeOH was kept at 80% in the first 30 min, then increased to 100% in 25 min) to afford 7 (1.2 mg, 36%, t$_R$=23.0 min, broad): $^1$H NMR (400 MHz, CD$_3$OD) δ 8.13 (s, 1H), 5.85 (ddd, J=15.6, 7.2, 7.2 Hz, 1H), 5.73 (dd, J=6.8, 6.8 Hz, 1H), 5.62 (dd, J=15.2, 7.2 Hz, 1H), 5.06 (d, J=17.6 Hz, 1H), 4.66 (dd, J=6.0, 6.0 Hz, 1H), 4.63 (br s, 1H), 4.41 (d, J=17.6 Hz, 1H), 3.96 (d, J=11.6 Hz, 1H), 3.42 (d, J=11.6 Hz, 1H), 3.10 (dd, J=17.2, 11.2 Hz, 1H), 2.80 (dd, J=19.2, 2.0 Hz, 1H), 2.76 (m, 2H), 2.56 (dd, J=6.8, 6.8 Hz, 2H), 2.36 (ddd, J=6.4, 6.4, 6.4 Hz, 2H), 1.94 (m, 2H), 1.81 (s, 3H).

Preparation of Compound 10

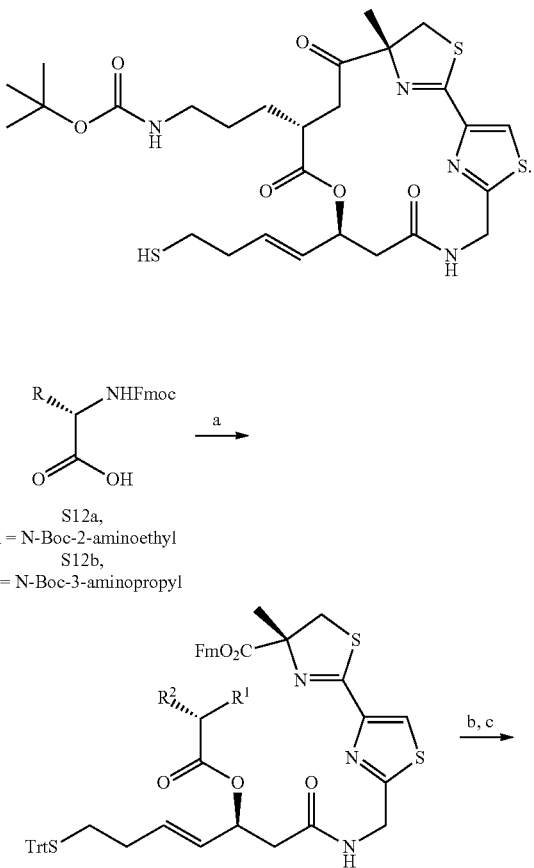

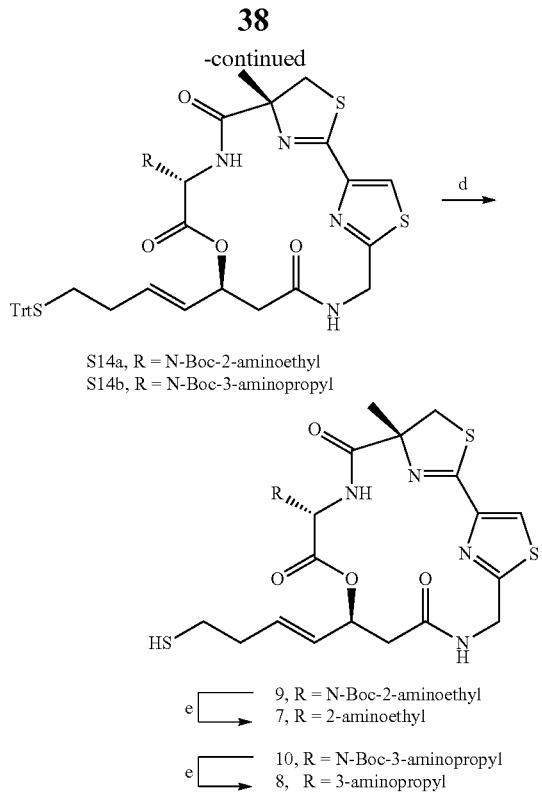

To a cooled (0° C.) solution of S12b (118.6 mg, 0.261 mmol) in THF (10 mL) were added 2,4,6-trichlorobenzoyl chloride (61.1 μL, 0.391 mmol) and Et$_3$N (63.7 μL, 0.457 mmol). After stirring for 2 h at 0° C., S8 (109 mg, 0.130 mmol) in THF (4 mL) and DMAP (31.9 mg, 0.261 mmol) were added at 0° C. After stirring for 1 h at 25° C., the reaction was quenched by the addition of saturated NH$_4$Cl solution and diluted with EtOAc. The layers were separated and the aqueous layer was extracted with EtOAc. The combined organic layers were dried over anhydrous Na$_2$SO$_4$ and concentrated in vacuo. The residue was purified by column chromatography (silica gel, EtOAc/hexanes=1/1) to afford S13b (146.4 mg, 83%): $^1$H NMR (400 MHz, CDCl$_3$) δ 7.84 (s, 1H), 7.72 (d, J=7.6 Hz, 4H), 7.57 (d, J=6.8 Hz, 4H), 7.17-7.39 (m, 23H), 5.55-5.67 (m, 2H), 5.40 (dd, J=15.2, 7.2 Hz, 1H), 4.66 (s, 2H), 4.47 (d, J=6.8 Hz, 2H), 4.14-4.33 (m, 5H), 3.67 (d, J=11.2 Hz, 1H), 3.18 (d, J=11.2 Hz, 1H), 3.05 (dd, J=5.6, 5.6 Hz, 2H), 2.55 (br s, 2H), 2.19 (dd, J=6.4, 6.4 Hz, 2H), 2.04 (d, J=7.2 Hz, 2H), 1.75 (br s, 4H), 1.58 (s, 3H), 1.42 (s, 9H).

To a solution of S13b (51.6 mg, 0.038 mmol) in CH$_3$CN (20 mL) was added Et$_2$NH (2 mL) at 25° C. After stirring for 2 h at 25° C., the reaction mixture was concentrated in vacuo and washed with toluene. After removal of toluene in vacuo, to a solution of the crude mixture in CH$_2$Cl$_2$ (43.4 mL) were added HATU (29.1 mg, 0.076 mmol) and i-Pr$_2$NEt (20 μL, 0.115 mmol) at 25° C. After stirring for 36 h at 25° C., the reaction mixture was concentrated in vacuo. The residue was diluted with H$_2$O and EtOAc. The layers were separated and the aqueous layer was extracted with EtOAc. The combined organic layers were dried over anhydrous Na$_2$SO$_4$ and concentrated in vacuo. The residue was purified by column chromatography (silica gel, EtOAc/hexanes/MeOH=30/30/1) to afford S14b (10.7 mg, 33% for two steps): $^1$H NMR (400 MHz, CD$_3$OD) δ 8.09 (s, 1H), 7.38 (d, J=8.0 Hz, 6H), 7.28 (dd, J=7.2, 7.2 Hz, 6H), 7.21 (dd, J=8.4, 8.4 Hz, 3H), 6.20 (br s, 1H), 5.71 (ddd, J=15.2, 7.2, 7.2 Hz, 1H), 5.65 (dd, J=12.4, 12.4 Hz, 1H), 5.47 (dd, J=15.6, 7.2 Hz, 1H), 5.07 (d, J=18.0 Hz, 1H), 4.55 (dd, J=4.8, 4.8 Hz, 1H), 4.36 (d, J=18.0 Hz, 1H), 3.98 (d, J=11.6 Hz, 1H), 3.35 (d, J=11.6 Hz, 1H), 2.99 (dd, J=16.8, 11.2 Hz, 1H), 2.75 (m, 2H), 2.70 (dd, J=16.8, 2.8 Hz, 1H), 2.20 (dd, J=6.8, 6.8 Hz, 2H), 2.06 (dd, J=7.6, 7.6 Hz, 2H), 1.78 (s, 3H), 1.70 (m, 2H), 1.41 (s, 9H).

To a cooled (0° C.) solution of S14b (10.7 mg, 0.0125 mmol) in CH$_2$Cl$_2$ (2 mL) were added TFA (200 μL) and i-Pr$_3$SiH (5 μL, 0.0149 mmol). After stirring for 15 min at 0° C., the reaction mixture was concentrated in vacuo. The residue was purified by column chromatography (silica gel, EtOAc/hexanes/MeOH=10/10/1) to afford 10 (4.8 mg, 63%): $^1$H NMR (400 MHz, CD$_3$OD) δ 8.10 (s, 1H), 7.40 (d, J=8.0 Hz, 1H), 5.83 (ddd, J=14.8, 7.2, 7.2 Hz, 1H), 5.59-5.70 (m, 2H), 5.09 (d, J=17.6 Hz, 1H), 4.57 (dd, J=4.8, 4.8 Hz, 1H), 4.40 (d, J=17.6 Hz, 1H), 3.98 (d, J=11.2 Hz, 1H), 3.36 (d, J=11.2 Hz, 1H), 3.05 (dd, J=16.8, 10.8 Hz, 1H), 2.72-2.78 (m, 3H), 2.55 (dd, J=6.4, 6.4 Hz, 2H), 2.35 (ddd, J=6.8, 6.8, 6.8 Hz, 2H), 1.80 (s, 3H), 1.70 (m, 2H), 1.41 (s, 9H).

Preparation of Compound 8

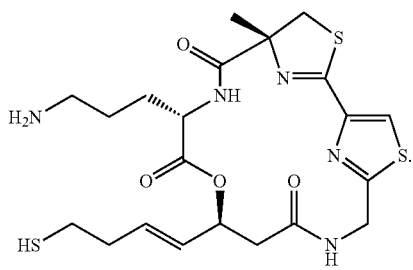 [SMILES: C[C@@]12CSC(=N1)c1csc(n1)CNC(=O)C[C@@H](/C=C/CCS)OC(=O)[C@H](CCCN)NC2=O]

To a solution of 10 (4.0 mg, 0.0065 mmol) in CH$_2$Cl$_2$ (0.1 mL) was added TFA (10 μL). The reaction mixture was stirred for 1 h at 25° C. until there was no more starting material left (detected by MS). The reaction mixture was purged with N$_2$ and dried in vacuo to remove TFA and CH$_2$Cl$_2$. The crude mixture was purified by HPLC (Syringe-Hydro RP, 4 μm, flow rate 2.0 mL/min) eluting with of MeOH/H$_2$O (MeOH was kept at 80% in the first 30 min, then increased to 100% in 25 min) to afford 8 (1.5 mg, 40%, t$_R$=23.0 min, broad): $^1$H NMR (400 MHz, CD$_3$OD) δ 8.12 (s, 1H), 5.85 (ddd, J=15.2, 6.8, 6.8 Hz, 1H), 5.60-5.73 (m, 2H), 5.06 (d, J=17.6 Hz, 1H), 4.62 (br s, 1H), 4.59 (dd, J=5.2, 5.2 Hz, 1H), 4.42 (d, J=17.6 Hz, 1H), 3.97 (d, J=11.6 Hz, 1H), 3.39 (d, J=11.6 Hz, 1H), 3.10 (dd, J=17.2, 10.8 Hz, 1H), 2.80 (dd, J=14.8, 1.2, 1H), 2.73 (dd, J=8.0, 8.0 Hz, 2H), 2.56 (dd, J=6.8, 6.8 Hz, 2H), 2.36 (ddd, J=7.2, 7.2, 7.2 Hz, 2H), 1.88 (m, 2H), 1.80 (s, 3H), 1.74 (m, 2H).

Preparation of Compound 11

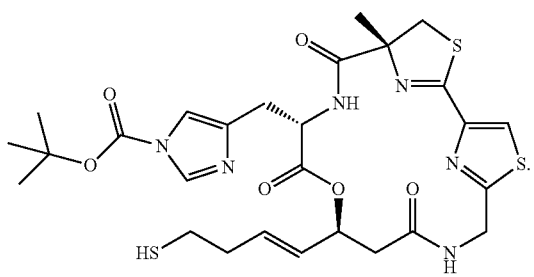

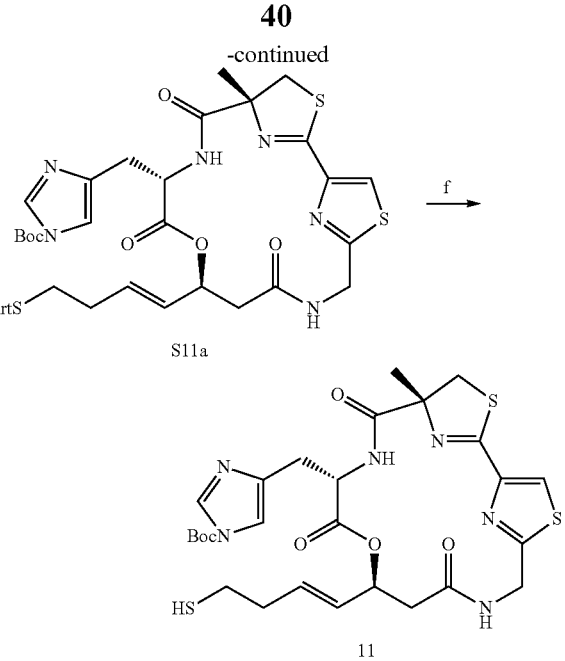

To a cooled (0° C.) solution of S11a (8.4 mg, 0.00958 mmol) in CH$_2$Cl$_2$ (1 mL) were added TFA (50 μL) and i-Pr$_3$SiH (4 μL, 0.0192 mmol). After stirring for 15 min at 0° C., the reaction mixture was concentrated in vacuo. The residue was purified by column chromatography (silica gel, EtOAc 100%) to afford 11 (2.7 mg, 44%): $^1$H NMR (400 MHz, CD$_3$OD) δ 8.03 (s, 1H), 7.51 (s, 1H), 7.37 (d, J=8.0 Hz, 1H), 6.93 (s, 1H), 5.83 (ddd, J=15.6, 6.4, 6.4 Hz, 1H), 5.71 (dd, J=8.0, 8.0 Hz, 1H), 5.62 (dd, J=15.2, 6.8 Hz, 1H), 5.09 (d, J=17.6, 1H), 4.76 (ddd, J=8.0, 4.4, 4.4 Hz, 1H), 4.37 (d, J=17.6 Hz, 1H), 3.89 (d, J=11.6 Hz, 1H), 3.35 (d, J=11.6 Hz, 1H), 3.06 (dd, J=14.8, 5.2 Hz, 1H), 2.99 (dd, J=16.0, 4.8 Hz, 1H), 2.97 (dd, J=9.6, 6.0 Hz, 1H), 2.70 (dd, J=17.2, 2.4 Hz, 1H), 2.55 (dd, J=6.8, 6.8 Hz, 2H), 2.35 (ddd, J=7.2, 7.2, 7.2 Hz, 2H), 1.75 (s, 3H), 1.60 (s, 9H).

Preparation of Compound 12

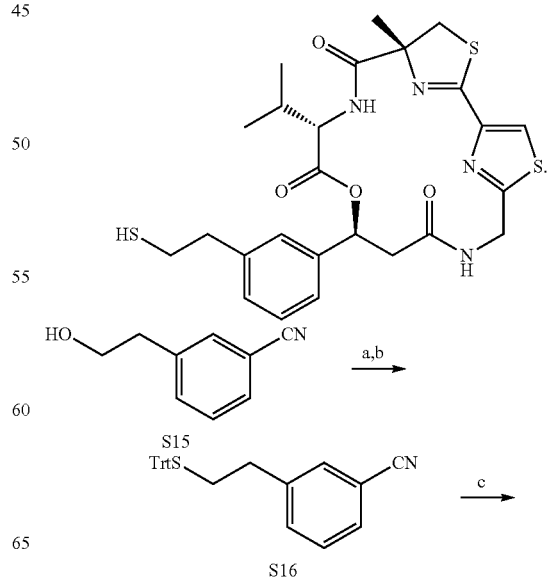

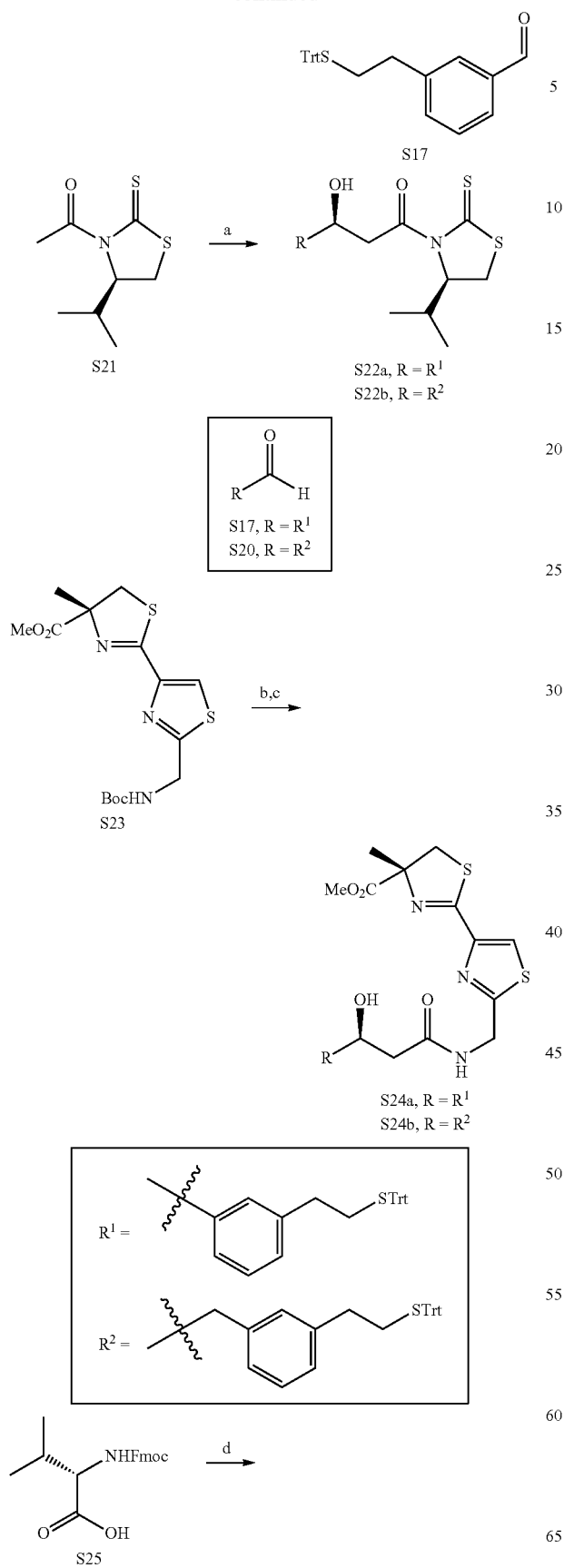
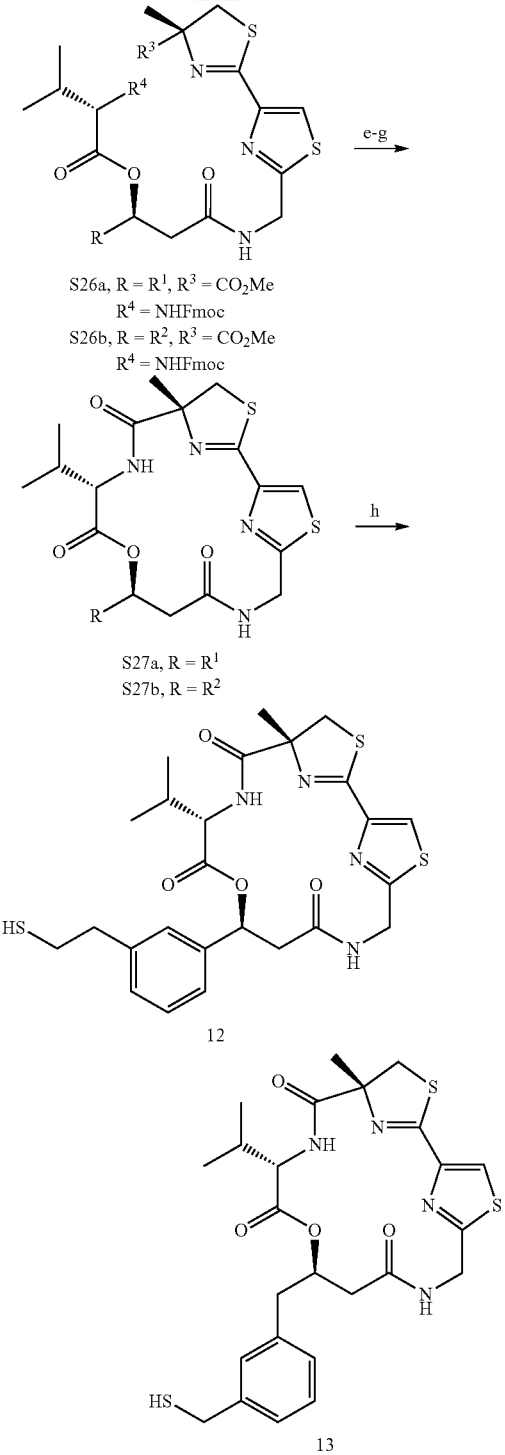

To a cooled (0° C.) solution of S15 (150 mg, 1.019 mmol) (which was prepared as described in Lee, B. C.; Choe, Y. S.; Lee, K. H.; Kim, B. T.; Chi, D. Y. J. *Labelled Compd. Rad.* 2001, 44, 5404) in $CH_2Cl_2$ (8 mL) were added MsCl (0.16 mL, 2.038 mmol) and $Et_3N$ (0.43 mL, 3.057 mmol). After stirring for 0.5 h at 0° C., brine was added. The layers were separated and the aqueous layer was extracted with $CH_2Cl_2$. The combined organic layers were dried over anhydrous $Na_2SO_4$ and concentrated in vacuo. To a cooled (0° C.) solution of the crude mixture in THF/DMF (4/1, 15 mL)

were added triphenylmethylsilane (TrtSH) (1.13 g, 4.076 mmol) and NaH (60% dispersion in mineral oil, 163 mg, 4.076 mmol). After stirring for 16 h at 25° C., the reaction mixture was quenched by the addition of saturated NH$_4$Cl solution and diluted with EtOAc. The layers were separated and the aqueous layer was extracted with EtOAc. The combined organic layers were dried over anhydrous Na$_2$SO$_4$ and concentrated in vacuo. The residue was purified by column chromatography (silica gel, EtOAc/hexanes=1/30) to afford S16 (1.8 g, 94% for two steps): $^1$H NMR (400 MHz, CDCl$_3$) δ 7.45-7.69 (m, 19H), 2.80 (dd, J=7.6, 7.6 Hz, 2H), 2.68 (dd, J=7.6, 7.6 Hz, 2H).

To a cooled (0° C.) solution of S16 (1.8 g, 4.44 mmol) in toluene (8 mL) was added 1.0 M DIBAL-H (2.0 mL, 2.038 mmol). After stirring for 1 h at 0° C., the reaction mixture was quenched by the addition of 1.0 N HCl solution and diluted with CH$_2$Cl$_2$ and H$_2$O. The layers were separated and the aqueous layer was extracted with CH$_2$Cl$_2$. The combined organic layers were dried over anhydrous Na$_2$SO$_4$ and concentrated in vacuo. The residue was purified by column chromatography (silica gel, EtOAc/hexanes=1/30) to afford S17 (208 mg, 57%): $^1$H NMR (400 MHz, CDCl$_3$) δ 9.95 (s, 1H), 7.69 (d, J=7.6 Hz, 1H), 7.49 (s, 1H), 7.19-7.41 (m, 17H), 2.63 (dd, J=7.6, 7.6 Hz, 2H), 2.47 (dd, J=7.6, 7.6 Hz, 2H).

To a cooled (−78° C.) solution of S21 (100 mg, 0.492 mmol) (which was prepared as described in Nagao, Y.; Hagiwara, Y.; Kumagai, T.; Ochiai, M.; Inoue, T.; Hashimoto, K.; Fujita, E. *J. Org. Chem.* 1986, 51, 2391) in CH$_2$Cl$_2$ (10 mL) was added 1.0 M TiCl$_4$ (0.6 mL, 0.600 mmol). After stirring for 5 min at −78° C., i-Pr$_2$NEt (0.1 mL, 0.596 mmol) was added slowly. The resulting mixture was stirred for 1 h at −78° C. before the addition of S17 (61 mg, 0.149 mmol) in CH$_2$Cl$_2$ (3 mL). After stirring for 1 h at −78° C., the reaction was quenched by the addition of saturated NH$_4$Cl solution. The layers were separated and the aqueous layer was extracted with CH$_2$Cl$_2$. The combined organic layers were dried over anhydrous Na$_2$SO$_4$ and concentrated in vacuo. The residue was purified by column chromatography (silica gel, EtOAc/hexanes=1/5 to 1/3) to afford S22a (64 mg, 70%): $^1$H NMR (400 MHz, CDCl$_3$) δ 7.40 (d, J=7.6 Hz, 6H), 7.24-7.31 (m, 6H), 7.17-7.23 (m, 5H), 7.02 (s, 1H), 6.91 (d, J=6.4 Hz, 1H), 5.21 (dd, J=9.2, 2.4 Hz, 1H), 5.12 (dd, J=6.8, 6.8 Hz, 1H), 3.73 (dd, J=17.2, 2.8 Hz, 1H), 3.56 (dd, J=17.2, 9.2 Hz, 1H), 3.46 (dd, J=11.6, 8.0 Hz, 1H), 3.11 (br s, 1H), 3.01 (dd, J=11.6, 0.8 Hz, 1H), 2.58 (m, 2H), 2.45 (m, 2H), 2.39 (m, 1H), 1.06 (d, J=6.8 Hz, 3H), 0.99 (d, J=6.8 Hz, 3H).

To a solution of S23 (58 mg, 0.157 mmol) (which was prepared as described in Ying, Y.; Taori, K.; Kim, H.; Hong, J.; Luesch, H. *J. Am. Chem. Soc.* 2008, 130, 8455) in CH$_2$Cl$_2$ (3 mL) was added TFA (1 mL) at 25° C. After stirring for 2 h at 25° C., the reaction mixture was concentrated in vacuo and washed with Et$_2$O. To a solution of the crude mixture in CH$_2$Cl$_2$ (10 mL) were added S22a (64 mg, 0.104 mmol) in CH$_2$Cl$_2$ (2 mL) and DMAP (64 mg, 0.520 mmol) at 25° C. After stirring for 2 h at 25° C., the reaction was quenched by the addition of H$_2$O. The layers were separated and the aqueous layer was extracted with CH$_2$Cl$_2$. The combined organic layers were dried over anhydrous Na$_2$SO$_4$ and concentrated in vacuo. The residue was purified by column chromatography (silica gel, EtOAc/hexanes/MeOH=10/10/1) to afford S24a (65 mg, 87% for two steps): $^1$H NMR (400 MHz, CDCl$_3$) δ 7.88 (s, 1H), 7.35-7.38 (m, 6H), 7.05-7.26 (m, 12H), 6.96 (s, 1H), 6.85 (d, J=7.2 Hz, 1H), 5.03 (dd, J=9.2, 3.2 Hz, 1H), 4.66 (m, 2H), 3.83 (d, J=11.2 Hz, 1H), 3.74 (s, 3H), 3.23 (d, J=11.2 Hz, 1H), 2.55 (m, 4H), 2.40 (dd, J=7.6, 7.6 Hz, 2H), 1.60 (s, 3H).

To a cooled (0° C.) solution of S25 (43 mg, 0.126 mmol) in THF (10 mL) were added 2,4,6-trichlorobenzoyl chloride (21 μL, 0.135 mmol) and Et$_3$N (20 μL, 0.144 mmol). After stirring for 2 h at 0° C., S24a (65 mg, 0.090 mmol) in THF (4 mL) and DMAP (13 mg, 0.108 mmol) were added at 0° C. After stirring for 2 h at 25° C., the reaction was quenched by the addition of saturated NH$_4$Cl solution and diluted with EtOAc. The layers were separated and the aqueous layer was extracted with EtOAc. The combined organic layers were dried over anhydrous Na$_2$SO$_4$ and concentrated in vacuo. The residue was purified by column chromatography (silica gel, EtOAc/hexanes/MeOH=2/1/0 to 10/10/1) to afford S26a (80 mg, 85%): $^1$H NMR (400 MHz, CDCl$_3$) δ 7.91 (s, 1H), 7.77 (d, J=7.6 Hz, 2H), 7.61 (d, J=7.2 Hz, 2H), 7.17-7.43 (m, 21H), 7.01 (s, 1H), 6.92 (m, 1H), 6.85 (m, 1H), 6.21 (dd, J=8.4, 4.8 Hz, 1H), 5.38 (d, J=8.8 Hz, 1H), 4.68 (d, J=5.6 Hz, 2H), 4.30 (m, 2H), 4.23 (m, 2H), 3.87 (d, J=11.2 Hz, 1H), 3.80 (s, 3H), 3.26 (d, J=11.6 Hz, 1H), 2.93 (dd, J=14.8, 8.8 Hz, 1H), 2.71 (dd, J=15.2, 4.8 Hz, 1H), 2.56 (m, 2H), 2.44 (m, 2H), 2.05 (m, 1H), 1.66 (s, 3H), 0.83 (d, J=6.8 Hz, 3H), 0.69 (d, J=6.4 Hz, 3H).

To a cooled (0° C.) solution of S26a (80 mg, 0.076 mmol) in THF/H$_2$O (4/1, 1.5 mL) was added 0.25 N LiOH (360 μL). After stirring for 2 h at 0° C., the reaction mixture was acidified by 0.25 N KHSO$_4$ until the pH of the solution reached 3. After dilution with EtOAc, the layers were separated and the aqueous layer was extracted with EtOAc. The combined organic layers were dried over anhydrous Na$_2$SO$_4$ and concentrated in vacuo. To a solution of the crude mixture in CH$_3$CN (8 mL) was added Et$_2$NH (2.0 mL) at 25° C. After stirring for 2 h at 25° C., the reaction mixture was concentrated in vacuo and washed with toluene. After removal of toluene in vacuo, to a solution of the crude mixture in CH$_2$Cl$_2$ (86.0 mL) were added HATU (58 mg, 0.152 mmol) and i-Pr$_2$NEt (40 μL, 0.228 mmol) at 25° C. After stirring for 24 h at 25° C., the reaction mixture was concentrated in vacuo. The residue was diluted with H$_2$O and EtOAc. The layers were separated and the aqueous layer was extracted with EtOAc. The combined organic layers were dried over anhydrous Na$_2$SO$_4$ and concentrated in vacuo. The residue was purified by column chromatography (silica gel, EtOAc/hexanes/MeOH=10/10/1) to afford S27a (14 mg, 23% for three steps): $^1$H NMR (400 MHz, CDCl$_3$) δ 7.75 (s, 1H), 7.32-7.34 (m, 6H), 7.12-7.27 (m, 11H), 7.05 (d, J=7.6 Hz, 1H), 6.97 (s, 1H), 6.82 (d, J=7.6 Hz, 1H), 6.25 (m, 1H), 6.02 (dd, J=10.8, 2.4 Hz, 1H), 5.25 (dd, J=17.2, 9.6 Hz, 1H), 4.49 (dd, J=9.6, 3.6 Hz, 1H), 4.15 (dd, J=17.2, 3.2 Hz, 1H), 4.02 (d, J=11.6 Hz, 1H), 3.26 (d, J=11.6 Hz, 1H), 3.00 (dd, J=16.0, 11.6 Hz, 1H), 2.68 (dd, J=16.4, 2.4 Hz, 1H), 2.49 (m, 2H), 2.37 (m, 2H), 2.06 (m, 1H), 1.84 (s, 3H), 0.63 (d, J=7.2 Hz, 3H), 0.49 (d, J=6.8 Hz, 3H).

To a cooled (0° C.) solution of S27a (13 mg, 0.017 mmol) in CH$_2$Cl$_2$ (3 mL) were added TFA (500 μL) and i-Pr$_3$SiH (7 μL, 0.033 mmol). After stirring for 1 h at 25° C., the reaction mixture was concentrated in vacuo. The residue was purified by column chromatography (silica gel, EtOAc/hexanes/MeOH=20/20/1) to afford 12 (5 mg, 55%): $^1$H NMR (500 MHz, CDCl$_3$) δ 7.80 (s, 1H), 7.28-7.32 (m, 2H), 7.24 (s, 1H), 7.18 (d, J=8.0 Hz, 1H), 7.13 (d, J=7.5 Hz, 1H), 6.33 (d, J=6.0 Hz, 1H), 6.15 (dd, J=10.5, 2.0 Hz, 1H), 5.31 (dd, J=17.5, 9.5 Hz, 1H), 4.57 (dd, J=9.5, 3.5 Hz, 1H), 4.25 (dd, J=17.5, 3.5 Hz, 1H), 4.07 (d, J=11.0 Hz, 1H), 3.31 (d, J=11.5 Hz, 1H), 3.10 (dd, J=16.5, 10.0 Hz, 1H), 2.90 (dd, J=8.0, 8.0 Hz, 2H), 2.80 (dd, J=16.5, 2.5 Hz, 1H), 2.76 (ddd, J=8.0, 8.0, 8.0 Hz, 2H), 2.11 (m, 1H), 1.91 (s, 3H), 1.34 (dd, J=8.0, 8.0 Hz, 1H), 0.70 (d, J=6.5 Hz, 3H), 0.57 (d, J=6.5 Hz, 3H).
Preparation of Compound 13
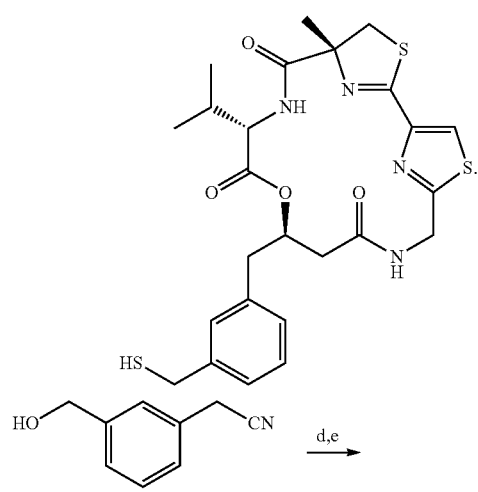
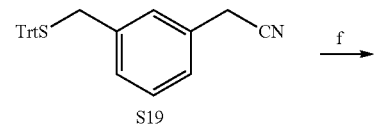
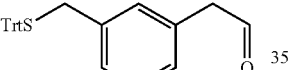
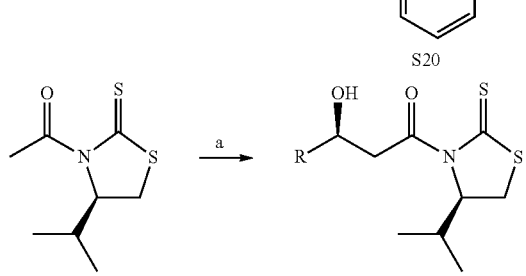
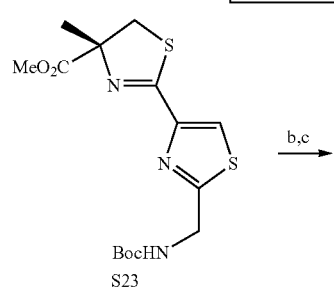
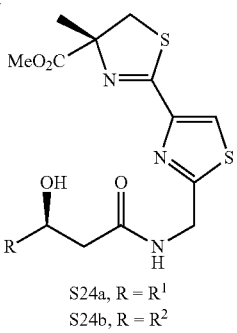
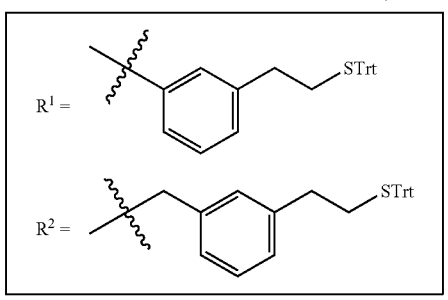
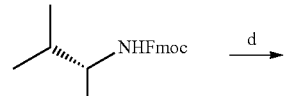
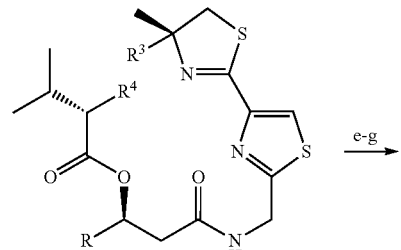
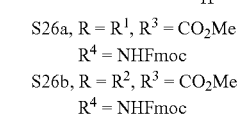
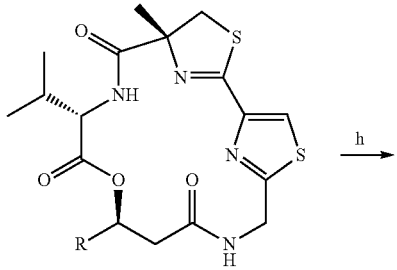

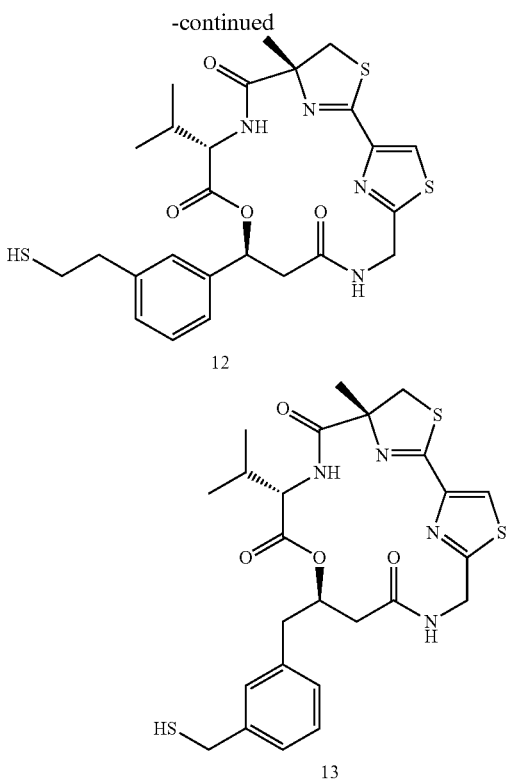

To a cooled (0° C.) solution of S18 (450 mg, 3.058 mmol) (which was prepared as described in Poverenov, E.; Gandelman, M.; Shimon, L. J. W.; Rozenberg, H.; Ben-David, Y.; Milstein, D. *Chem.—Eur. J.* 2004, 10, 4673) in $CH_2Cl_2$ (30 mL) were added $CBr_4$ (1.12 g, 3.363 mmol) and $PPh_3$ (882 mg, 3.363 mmol). After stirring for 1 h at 0° C., the reaction mixture was diluted with $H_2O$ and $CH_2Cl_2$. The layers were separated and the aqueous layer was extracted with $CH_2Cl_2$. The combined organic layers were dried over anhydrous $Na_2SO_4$ and concentrated in vacuo. The residue was purified by column chromatography (silica gel, EtOAc/hexanes=1/10) to afford the resulting intermediate in $EtOH/THF/H_2O$ (3/1/1, 30 mL) were added TrtSH (1.27 g, 4.587 mmol) and LiOH (110 mg, 4.587 mmol) at 25° C. After stirring for 2 h at 25° C., the reaction mixture was concentrated in vacuo. The residue was diluted with $CH_2Cl_2$ and $H_2O$. The layers were separated and the aqueous layer was extracted with $CH_2Cl_2$. The combined organic layers were dried over anhydrous $Na_2SO_4$ and concentrated in vacuo. The residue was purified by column chromatography (silica gel, EtOAc/hexanes=1/10) to afford S19 (1.14 g, 92% for two steps): $^1$H NMR (400 MHz, $CDCl_3$) δ 7.48-7.51 (m, 6H), 7.31-7.36 (m, 6H), 7.24-7.28 (m, 4H), 7.16 (d, J=7.6 Hz, 1H), 7.12 (d, J=7.6 Hz, 1H), 7.04 (s, 1H), 3.67 (s, 2H), 3.36 (s, 2H).

To a cooled (0° C.) solution of S19 (792 mg, 1.953 mmol) in toluene (20 mL) was added 1.0 M DIBAL-H (2.9 mL, 2.930 mmol). After stirring for 1 h at 0° C., the reaction mixture was quenched by the addition of 1.0 N HCl solution and diluted with $CH_2Cl_2$ and $H_2O$. The layers were separated and the aqueous layer was extracted with $CH_2Cl_2$. The combined organic layers were dried over anhydrous $Na_2SO_4$ and concentrated in vacuo to afford S20, which was employed in the next step without further purification. $^1$H NMR (400 MHz, $CDCl_3$) δ 9.69 (dd, J=2.4, 2.4 Hz, 1H), 7.45-7.48 (m, 6H), 7.28-7.33 (m, 6H), 7.21-7.26 (m, 4H), 7.08 (d, J=8.0 Hz, 1H), 7.05 (d, J=7.6 Hz, 1H), 6.93 (s, 1H), 3.61 (d, J=2.4 Hz, 2H), 3.32 (s, 2H).

To a cooled (−78° C.) solution of S21 (279 mg, 1.370 mmol) (which was prepared as described in Nagao, Y.; Hagiwara, Y.; Kumagai, T.; Ochiai, M.; Inoue, T.; Hashimoto, K.; Fujita, E. *J. Org. Chem.* 1986, 51, 2391) in $CH_2Cl_2$ (30 mL) in $CH_2Cl_2$ (15 mL) was added 1.0 M $TiCl_4$ (1.5 mL, 1.50 mmol). After stirring for 5 min at −78° C., i-$Pr_2NEt$ (0.26 mL, 1.508 mmol) was added slowly. The resulting mixture was stirred for 1 h at −78° C. before the addition of S20 (280 mg, 0.685 mmol) in $CH_2Cl_2$ (5 mL). After stirring for 1 h at −78° C., the reaction was quenched by the addition of saturated $NH_4Cl$ solution. The layers were separated and the aqueous layer was extracted with $CH_2Cl_2$. The combined organic layers were dried over anhydrous $Na_2SO_4$ and concentrated in vacuo. The residue was purified by column chromatography (silica gel, EtOAc/hexanes=1/5 to 1/3) to afford S22b (77 mg, 18% for two steps): $^1$H NMR (500 MHz, $CDCl_3$) δ 7.46-7.49 (m, 6H), 7.27-7.33 (m, 6H), 7.21-7.25 (m, 3H), 7.20 (dd, J=7.6, 7.6 Hz, 1H), 7.07 (d, J=7.6 Hz, 1H), 7.03 (d, J=7.6 Hz, 1H), 6.98 (s, 1H), 5.14 (dd, J=6.8, 6.8 Hz, 1H), 4.33 (m, 2H), 3.60 (dd, J=17.6, 2.4 Hz, 1H), 3.49 (dd, J=11.2, 8.0 Hz, 1H), 3.30 (s, 2H), 3.16 (dd, J=11.6, 9.2 Hz, 1H), 3.00 (d, J=11.2 Hz, 1H), 2.79 (m, 3H), 2.33 (m, 1H), 1.04 (d, J=6.8 Hz, 3H), 0.96 (d, J=6.8 Hz, 3H).

To a solution of S23 (80 mg, 0.215 mmol) (which was prepared as described in Ying, Y.; Taori, K.; Kim, H.; Hong, J.; Luesch, H. *J. Am. Chem. Soc.* 2008, 130, 8455) in $CH_2Cl_2$ (3 mL) was added TFA (1 mL) at 25° C. After stirring for 2 h at 25° C., the reaction mixture was concentrated in vacuo and washed with $Et_2O$. To a solution of the crude mixture in $CH_2Cl_2$ (5 mL) were added S22b (77 mg, 0.125 mmol) in $CH_2Cl_2$ (2 mL) and DMAP (76 mg, 0.625 mmol) at 25° C. After stirring for 2 h at 25° C., the reaction was quenched by the addition of $H_2O$. The layers were separated and the aqueous layer was extracted with $CH_2Cl_2$. The combined organic layers were dried over anhydrous $Na_2SO_4$ and concentrated in vacuo. The residue was purified by column chromatography (silica gel, EtOAc/hexanes/MeOH=10/10/1) to afford S24b (78 mg, 85% for two steps): $^1$H NMR (400 MHz, $CDCl_3$) δ 7.90 (s, 1H), 7.44-7.48 (m, 6H), 7.27-7.32 (m, 6H), 7.20-7.25 (m, 3H), 7.17 (dd, J=7.6, 7.6 Hz, 1H), 6.98-7.03 (m, 3H), 6.94 (s, 1H), 4.72 (dd, J=16.0, 6.0 Hz, 1H), 4.65 (dd, J=16.0, 6.0 Hz, 1H), 4.19 (m, 1H), 3.84 (d, J=11.2 Hz, 1H), 3.79 (s, 3H), 3.29 (s, 2H), 3.24 (d, J=11.2 Hz, 1H), 2.77 (dd, J=13.2, 7.6 Hz, 1H), 2.69 (dd, J=13.6, 6.0 Hz, 1H), 2.41 (dd, J=15.2, 2.8 Hz, 1H), 2.31 (dd, J=15.2, 4.8 Hz, 1H), 1.61 (s, 3H).

To a cooled (0° C.) solution of S25 (51 mg, 0.151 mmol) in THF (10 mL) were added 2,4,6-trichlorobenzoyl chloride (26 μL, 0.162 mmol) and $Et_3N$ (24 μL, 0.173 mmol). After stirring for 2 h at 0° C., S24b (78 mg, 0.108 mmol) in THF (4 mL) and DMAP (13 mg, 0.108 mmol) were added at 0° C. After stirring for 2 h at 25° C., the reaction was quenched by the addition of saturated $NH_4Cl$ solution and diluted with EtOAc. The layers were separated and the aqueous layer was extracted with EtOAc. The combined organic layers were dried over anhydrous $Na_2SO_4$ and concentrated in vacuo. The residue was purified by column chromatography (silica gel, EtOAc/hexanes/MeOH=2/1/0 to 10/10/1) to afford S26b (105 mg, 93%): $^1$H NMR (400 MHz, $CDCl_3$) δ 7.92 (s, 1H), 7.77 (d, J=7.6 Hz, 2H), 7.61 (d, J=7.2 Hz, 2H), 7.44-7.48 (m, 6H), 7.19-7.33 (m, 14H), 7.16 (dd, J=7.6, 7.6 Hz, 1H), 6.98-7.03 (m, 3H), 6.93 (s, 1H), 6.21 (m, 1H), 5.41 (m, 1H), 4.70 (d, J=6.0 Hz, 2H), 4.30 (m, 2H), 4.23 (m, 2H), 3.87 (d, J=11.2 Hz, 1H), 3.78 (s, 3H), 3.31 (s, 2H), 3.25 (d, J=11.6 Hz, 1H), 2.77 (dd, J=13.2, 7.6 Hz, 1H), 2.69 (dd, J=13.6, 6.0

Hz, 1H), 2.41 (dd, J=15.2, 2.8 Hz, 1H), 2.31 (dd, J=15.2, 4.8 Hz, 1H), 2.06 (m, 1H), 1.67 (s, 3H), 0.84 (d, J=6.8 Hz, 3H), 0.67 (d, J=6.8 Hz, 3H).

To a cooled (0° C.) solution of S26b (105 mg, 0.101 mmol) in THF/H$_2$O (4/1, 1.5 mL) was added 0.25 N LiOH (480 μL). After stirring for 2 h at 0° C., the reaction mixture was acidified by 0.25 N KHSO$_4$ until the pH of the solution reached 3. After dilution with EtOAc, the layers were separated and the aqueous layer was extracted with EtOAc. The combined organic layers were dried over anhydrous Na$_2$SO$_4$ and concentrated in vacuo. To a solution of the crude mixture in CH$_3$CN (10 mL) was added Et$_2$NH (2.0 mL) at 25° C. After stirring for 2 h at 25° C., the reaction mixture was concentrated in vacuo and washed with toluene. After removal of toluene in vacuo, to a solution of the crude mixture in CH$_2$Cl$_2$ (115.0 mL) were added HATU (77 mg, 0.202 mmol) and i-Pr$_2$NEt (53 μL, 0.303 mmol) at 25° C. After stirring for 24 h at 25° C., the reaction mixture was concentrated in vacuo. The residue was diluted with H$_2$O and EtOAc. The layers were separated and the aqueous layer was extracted with EtOAc. The combined organic layers were dried over anhydrous Na$_2$SO$_4$ and concentrated in vacuo. The residue was purified by column chromatography (silica gel, EtOAc/hexanes/MeOH=10/10/1) to afford S27b (31 mg, 39% for three steps): $^1$H NMR (400 MHz, CDCl$_3$) δ 7.75 (s, 1H), 7.45-7.48 (m, 6H), 7.31 (dd, J=7.6, 7.6 Hz, 6H), 7.19-7.25 (m, 3H), 7.18 (dd, J=7.6, 7.6 Hz, 1H), 7.11 (d, J=9.6 Hz, 1H), 7.02-7.05 (m, 2H), 6.90 (s, 1H), 6.24 (dd, J=9.2, 3.2 Hz, 1H), 5.42 (m, 1H), 5.21 (dd, J=17.6, 9.2 Hz, 1H), 4.68 (dd, J=9.2, 3.2 Hz, 1H), 4.19 (dd, J=17.6, 3.2 Hz, 1H), 4.05 (d, J=11.6 Hz, 1H), 3.30 (s, 2H), 3.27 (d, J=11.6 Hz, 1H), 3.22 (dd, J=13.6, 4.0 Hz, 1H), 2.63 (dd, J=12.8, 9.2 Hz, 1H), 2.62 (dd, J=16.4, 10.8 Hz, 1H), 2.53 (dd, J=16.4, 2.8 Hz, 1H), 2.19 (m, 1H), 1.85 (s, 3H), 0.71 (d, J=7.2 Hz, 3H), 0.50 (d, J=6.8 Hz, 3H).

To a cooled (0° C.) solution of S27b (19 mg, 0.024 mmol) in CH$_2$Cl$_2$ (3 mL) were TFA (500 μL) and i-Pr$_3$SiH (10 μL, 0.033 mmol). After stirring for 1 h at 25° C., the reaction mixture was concentrated in vacuo. The residue was purified by column chromatography (silica gel, EtOAc/hexanes/MeOH=15/15/1) to afford 13 (11 mg, 84%): $^1$H NMR (400 MHz, CDCl$_3$) δ 7.76 (s, 1H), 7.19-7.25 (m, 2H), 7.16 (s, 1H), 7.07-7.12 (m, 2H), 6.27 (dd, J=9.6, 2.8 Hz, 1H), 5.46 (m, 1H), 5.22 (dd, J=17.6, 9.6 Hz, 1H), 4.69 (dd, J=9.6, 3.2 Hz, 1H), 4.22 (dd, J=17.6, 3.6 Hz, 1H), 4.05 (d, J=11.2 Hz, 1H), 3.71 (d, J=7.6 Hz, 2H), 3.27 (d, J=11.2 Hz, 1H), 3.23 (dd, J=13.6, 4.0 Hz, 1H), 2.76 (dd, J=13.2, 8.8 Hz, 1H), 2.68 (dd, J=16.4, 10.4 Hz, 1H), 2.60 (dd, J=16.4, 3.2 Hz, 1H), 2.17 (m, 1H), 1.86 (s, 3H), 1.77 (dd, J=7.6, 7.6 Hz, 1H), 0.70 (d, J=6.8 Hz, 3H), 0.50 (d, J=7.2 Hz, 3H).

Preparation of Compound 14

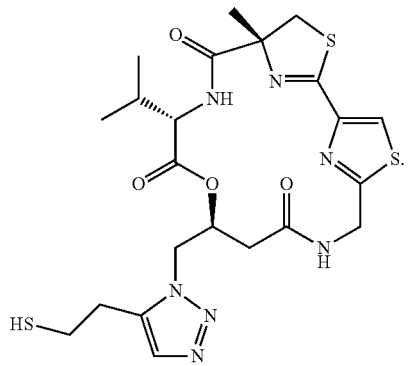

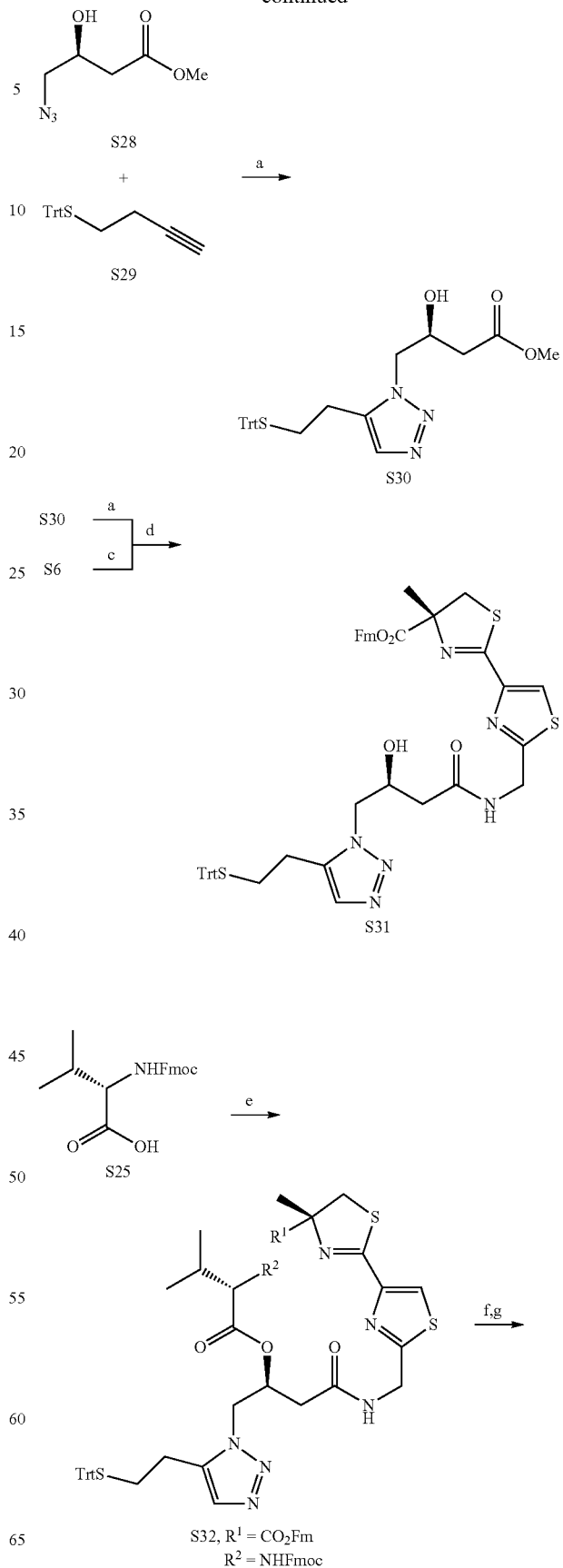

-continued

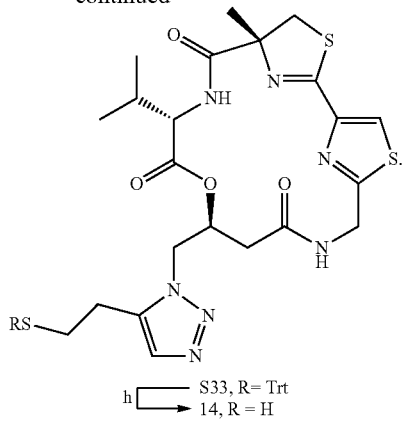

h ⎡ S33, R= Trt
  ⎣→ 14, R = H

To a solution of S28 (280 mg, 1.759 mmol) (which was prepared as described in Nakatani, S.; Ikura, M.; Yamamoto, S.; Nishita, Y.; Itadani, S.; Habashita, H.; Sugiura, T.; Ogawa, K.; Ohno, H.; Takahashi, K.; Nakai, H.; Toda, M. Bioorg. Med. Chem. 2006, 14, 5402) and S29 (867 mg, 2.639 mmol) in benzene (20 mL) was added Cp*RuCl(PPh₃)₂ (28 mg, 0.035 mmol) at 25° C. After refluxing for 12 h, the reaction mixture was concentrated in vacuo. The residue was purified by column chromatography (silica gel, EtOAc/hexanes/MeOH=15/15/1) to afford S30 (484 mg, 56%): ¹H NMR (400 MHz, CDCl₃) δ 7.40-7.42 (m, 6H), 7.21-7.32 (m, 10H), 4.43 (m, 1H), 4.23 (dd, J=14.0, 3.6 Hz, 1H), 4.09 (dd, J=14.0, 7.2 Hz, 1H), 3.70 (s, 3H), 2.59-2.66 (m, 2H), 2.46-2.66 (m, 4H).

To a solution of S30 (90 mg, 0.185 mmol) in THF/H₂O (4/1, 6 mL) was added 1.0 N LiOH (370 μL) at 25° C. After stirring for 2 h at 25° C., the reaction mixture was acidified by 1.0 N KHSO₄ solution. After dilution with EtOAc, the layers were separated and the aqueous layer was extracted with EtOAc. The combined organic layers were dried over anhydrous Na₂SO₄ and concentrated in vacuo. To a solution of S6 (132 mg, 0.241 mmol) in CH₂Cl₂ (10 mL) was added TFA (2.0 mL) at 25° C. After stirring for 2 h, the solvent was removed in vacuo and the mixture was washed with Et₂O. After dissolving the reaction mixture in CH₃CN (15 mL), PyBOP (193 mg, 0.370 mmol), DMAP (90 mg, 0.740 mmol), and the crude S30 were added at 25° C. After stirring for 4 h at 25° C., the reaction mixture was concentrated in vacuo. The residue was diluted with EtOAc and saturated NH₄Cl solution. The layers were separated and the aqueous layer was extracted with EtOAc. The combined organic layers were dried over anhydrous Na₂SO₄ and concentrated in vacuo. The residue was purified by column chromatography (silica gel, EtOAc/hexanes/MeOH=10/10/1) to afford S31 (147 mg, 89% for three steps): ¹H NMR (400 MHz, CDCl₃) δ 7.84 (s, 1H), 7.72 (dd, J=7.6, 4.4 Hz, 2H), 7.58 (dd, J=7.6, 3.2 Hz, 2H), 7.52 (dd, J=5.6, 5.6 Hz, 1H), 7.15-7.43 (m, 19H), 4.73 (dd, J=16.0, 6.0 Hz, 1H), 4.67 (dd, J=16.8, 6.0 Hz, 1H), 4.50 (d, J=6.4 Hz, 2H), 4.34 (m, 1H), 4.23 (dd, J=6.4, 6.4 Hz, 1H), 3.69 (d, J=11.2 Hz, 1H), 3.20 (d, J=11.2 Hz, 1H), 2.58 (dd, J=7.6, 7.6 Hz, 2H), 2.50 (dd, J=15.6, 4.0 Hz, 1H), 2.44 (dd, J=7.6, 7.6 Hz, 2H), 2.33 (dd, J=14.8, 8.4 Hz, 1H), 1.57 (s, 3H).

To a cooled (0° C.) solution of S25 (75 mg, 0.220 mmol) in THF (8 mL) were added 2,4,6-trichlorobenzoyl chloride (37 μL, 0.236 mmol) and Et₃N (35 μL, 0.251 mmol). After stirring for 1 h at 0° C., S31 (140 mg, 0.157 mmol) in THF (2 mL) and DMAP (23 mg, 0.188 mmol) were added at 0° C. After stirring for 2 h at 25° C., the reaction was quenched by the addition of saturated NH₄Cl solution and diluted with EtOAc. The layers were separated and the aqueous layer was extracted with EtOAc. The combined organic layers were dried over anhydrous Na₂SO₄ and concentrated in vacuo. The residue was purified by column chromatography (silica gel, EtOAc/hexanes/MeOH=15/15/1 to 10/10/1) to afford S32 (177 mg, 93%): ¹H NMR (400 MHz, CDCl₃) δ 7.93 (s, 1H), 7.73 (dd, J=6.4, 6.4 Hz, 4H), 7.61 (d, J=7.2 Hz, 2H), 7.54 (d, J=7.2 Hz, 2H), 7.19-7.41 (m, 24H), 5.59 (m, 1H), 5.29 (d, J=7.6 Hz, 1H), 4.77 (dd, J=6.0, 6.0 Hz, 2H), 4.43-4.53 (m, 4H), 4.39 (dd, J=10.4, 6.8 Hz, 1H), 4.33 (dd, J=10.4, 6.8 Hz, 1H), 4.24 (dd, J=6.8, 6.8 Hz, 1H), 4.17 (dd, J=6.8, 6.8 Hz, 1H), 3.93 (dd, J=6.4, 6.4 Hz, 1H), 3.74 (d, J=11.6 Hz, 1H), 3.19 (d, J=11.2 Hz, 1H), 2.74 (dd, J=14.8, 6.0 Hz, 1H), 2.45-2.66 (m, 6H), 1.88 (m, 1H), 1.64 (s, 3H), 3.19 (d, J=6.4 Hz, 6H).

To a solution of S32 (79 mg, 0.065 mmol) in CH₃CN (8 mL) was added Et₂NH (1.5 mL) at 25° C. After stirring for 2 h at 25° C., the reaction mixture was concentrated in vacuo and washed with toluene. After removal of toluene in vacuo, to a solution of the crude mixture in CH₂Cl₂ (74.0 mL) were added HATU (49 mg, 0.130 mmol) and i-Pr₂NEt (34 μL, 0.195 mmol) at 25° C. After stirring for 24 h at 25° C., the reaction mixture was concentrated in vacuo. The residue was diluted with H₂O and EtOAc. The layers were separated and the aqueous layer was extracted with EtOAc. The combined organic layers were dried over anhydrous Na₂SO₄ and concentrated in vacuo. The residue was purified by column chromatography (silica gel, EtOAc/hexanes/MeOH=10/10/1) to afford S33 (14 mg, 27% for two steps): ¹H NMR (500 MHz, CDCl₃) δ 7.74 (s, 1H), 7.38 (d, J=7.5 Hz, 6H), 7.34 (s, 1H), 7.28 (dd, J=7.5, 7.5 Hz, 6H), 7.21 (dd, J=7.0, 7.0 Hz, 3H), 7.06 (d, J=10.0 Hz, 1H), 6.72 (dd, J=9.0, 3.5 Hz, 1H), 5.31 (m, 1H), 5.21 (dd, J=17.5, 9.0 Hz, 1H), 4.66 (dd, J=9.0, 3.5 Hz, 1H), 4.53 (dd, J=14.0, 8.5 Hz, 1H), 4.40 (dd, J=14.0, 3.5 Hz, 1H), 4.25 (dd, J=17.5, 9.0 Hz, 1H), 4.01 (d, J=12.0 Hz, 1H), 3.28 (d, J=11.0 Hz, 1H), 2.78 (dd, J=16.0, 3.0 Hz, 1H), 2.72 (dd, J=16.5, 10.0 Hz, 1H), 2.68 (m, 1H), 2.58 (m, 1H), 2.46 (dd, J=7.0, 7.0 Hz, 2H), 2.14 (m, 1H), 1.82 (s, 3H), 0.73 (d, J=7.0 Hz, 3H), 0.54 (d, J=6.5 Hz, 3H).

To a cooled (0° C.) solution of S33 (14 mg, 0.0176 mmol) in CH₂Cl₂ (3 mL) were added TFA (500 μL) and i-Pr₃SiH (7 μL, 0.0352 mmol). After stirring for 1 h at 25° C., the reaction mixture was concentrated in vacuo. The residue was purified by column chromatography (silica gel, EtOAc/hexanes/MeOH=5/5/1) to afford 14 (7 mg, 72%): ¹H NMR (400 MHz, CDCl₃) δ 7.76 (s, 1H), 7.58 (s, 1H), 7.07 (d, J=9.6 Hz, 1H), 6.60 (dd, J=9.2, 3.2 Hz, 1H), 5.43 (m, 1H), 5.23 (dd, J=17.6, 9.2 Hz, 1H), 4.72 (dd, J=9.6, 3.6 Hz, 1H), 4.70 (dd, J=15.2, 7.6 Hz, 1H), 4.63 (dd, J=14.8, 3.6 Hz, 1H), 4.26 (dd, J=17.6, 3.6 Hz, 1H), 4.01 (d, J=11.2 Hz, 1H), 3.29 (d, J=11.6 Hz, 1H), 3.03 (ddd, J=7.2, 7.2, 2.8 Hz, 2H), 2.89 (dd, J=16.8, 3.2 Hz, 1H), 2.83 (m, 2H), 2.79 (dd, J=16.8, 10.4 Hz, 1H), 2.16 (m, 1H), 1.84 (s, 3H), 1.58 (dd, J=7.6, 7.6 Hz, 1H), 0.73 (d, J=6.8 Hz, 3H), 0.52 (d, J=6.8 Hz, 3H).

Example 2: HDAC Inhibition

Enzyme inhibitory assays were carried out essentially as follows. In brief, compounds were incubated with the appropriate HDAC enzyme, the appropriate HDAC substrate, bovine serum albumin, and HDAC buffer. Duplicate reactions were carried out at 37° C. for 30 min. The reactions were quenched at the end of the incubation period with the addition of HDAC developer. Reactions were further incubated for 15 min at room temperature prior to fluorescence measurement (ex 360 nm/em 460 nm). The % inhibitory activity was calculated according to the equation (F−Fb)/(Ft−Fb), where F—fluorescent intensity of compound treated wells, Fb—fluorescent intensity of blank wells, Ft—fluorescent intensity of solvent control wells. $IC_{50}$ values were calculated using GraphPad Prism.

The HDAC inhibition profile showed that 3-6 are very weak HDAC8 inhibitors, implying that the largazole scaffold has an intrinsic preference towards the inhibition of HDACs 1, 2, and 3 over HDAC8 (Table 1). Also, while 3-5 were comparable in potency to largazole thiol (2), aspartic acid analogue 6 experienced a significant reduction in activity. It is notable that there was an overall decrease in HDAC2 inhibition and that histidine analogue 5 showed selectivity towards HDAC1 over HDACs 2 and 3 (7- and 5.5-fold, respectively).

TABLE 1

Class I HDAC isoform selectivity of Compounds 3-6

| Compound | R | $IC_{50}$ (nM) HDAC1 | HDAC2 | HDAC3 | HDAC8 | $IC_{50}$ (HDAC2)/ $IC_{50}$ (HDAC1) | $IC_{50}$ (HDAC3)/ $IC_{50}$ (HDAC1) |
|---|---|---|---|---|---|---|---|
| 2 (Largazole) | isopropyl | 0.40 | 0.90 | 0.70 | 102 | 2.3 | 1.8 |
| 3 | benzyl | 0.29 | 1.70 | 0.68 | No Inhibition up to 1 μM | 5.9 | 2.3 |
| 4 | 4-hydroxybenzyl | 0.21 | 1.10 | 0.38 | No Inhibition up to 1 μM | 5.2 | 1.8 |
| 5 | imidazolylmethyl | 0.20 | 1.40 | 1.10 | No Inhibition up to 1 μM | 7.0 | 5.5 |
| 6 | carboxymethyl | 39 | 150 | 100 | No Inhibition up to 1 μM | 3.9 | 2.6 |

Compounds 7-10 were designed to mimic the position of the two different nitrogens present in the histidine moiety of Compound 5. As summarized in Table 2, compounds 7 and 8 showed decreased activity for all HDACs tested. However, the longer alkyl chain analogue 8 showed a higher potency than the shorter alkyl chain analogue 7 for HDACs 1, 2, and 3. The same trend was observed for the corresponding N-Boc protected analogues, as 10 was more potent than 9 for all HDACs tested. The N-Boc protected histidine analogue 11 showed very little change in potency or selectivity relative to the des-Boc Compound 5.

TABLE 2

Class I HDAC isoform selectivity of Compounds 7-11

[Structure: macrocyclic compound with thiazoline-thiazole, HS-(CH2)2-CH=CH- chain, and variable R group on amino acid residue]

| Compound | R | IC$_{50}$ (nM) HDAC1 | HDAC2 | HDAC3 | HDAC8 | IC$_{50}$ (HDAC2)/ IC$_{50}$ (HDAC1) | IC$_{50}$ (HDAC3)/ IC$_{50}$ (HDAC1) |
|---|---|---|---|---|---|---|---|
| 2 (Largazole) | isopropyl | 0.40 | 0.90 | 0.70 | 102 | 2.3 | 1.8 |
| 7 | -CH2-NH2 | 5.50 | 21.00 | 7.80 | No Inhibition up to 1 μM | 3.8 | 1.4 |
| 8 | -(CH2)2-NH2 | 3.30 | 6.30 | 6.00 | No Inhibition up to 1 μM | 1.9 | 1.8 |
| 9 | -CH2-NHBoc | 2.30 | 3.10 | 4.20 | No Inhibition up to 1 μM | 1.4 | 1.8 |
| 10 | -(CH2)2-NHBoc | 0.96 | 1.40 | 1.80 | 790 | 1.5 | 1.9 |
| 11 | -CH2-(N-Boc-imidazolyl) | 0.62 | 1.10 | 1.10 | 540 | 1.8 | 1.8 |

There are two phenylalanine residues (Phe150 and Phe205) in the active site of HDAC1. To utilize π-π stacking interactions for the improvement of HDAC1 selectivity, compounds 12-14 were prepared and evaluated for their class I HDAC inhibition. Compounds 12-14 showed reduced activity against class I HDACs.

REFERENCES (1) (a) Koehn, F. E.; Carter, G. T. *Nat. Rev. Drug Discov.* 2005, 4, 206-220. (b) Paterson, I.; Anderson, E. A. *Science* 2005, 310, 451-453.
(2) Fenical, W.; Jensen, P. R. *Nat. Chem. Biol.* 2006, 2, 666-673.
(3) Gerwick, W. H.; Tan, L. T.; Sitachitta, N. *Alkaloids Chem. Biol.* 2001, 57, 75-184.
(4) Luesch, H.; Moore, R. E.; Paul, V. J.; Mooberry, S. L.; Corbett, T. H. *J. Nat. Prod.* 2001, 64, 907-910.
(5) (a) Gerwick, W. H.; Proteau, P. J.; Nagle, D. G.; Hamel, E.; Blokhin, A.; Slate, D. L. *J. Org. Chem.* 1994, 59, 1243-1245. (b) Verdier-Pinard, P.; Lai, J.-Y.; Yoo, H.-D.; Yu, J.; Marquez, B.; Nagle, D. G.; Nambu, M.; White, J. D.; Falck, J. R.; Gerwick, W. H.; Day, B. W.; Hamel, E. *Mol. Pharmacol.* 1998, 53, 62-76.
(6) (a) Luesch, H.; Yoshida, W. Y.; Moore, R. E.; Paul, V. J.; Corbett, T. H. *J. Am. Chem. Soc.* 2001, 123, 5418-5423. (b) Luesch, H.; Chanda, S. K.; Raya, M. R.; DeJesus, P. D.; Orth, A. P.; Walker, J. R.; Izpisúa Belmonte, J. C.; Schultz, P. G. *Nat. Chem. Biol.* 2006, 2, 158-167.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:
1. A compound according to Formulae I or II:

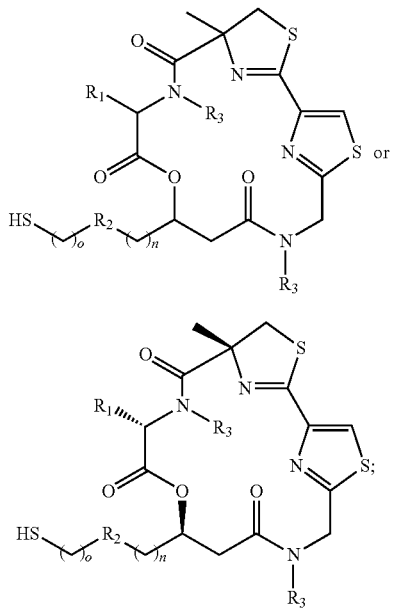

wherein:
each $R_1$ is independently optionally substituted arylalkyl, optionally substituted heteroarylalkyl, optionally substituted carboxyalkyl, or optionally substituted aminoalkyl;
each $R_2$ is independently optionally substituted alkenylene, optionally substituted arylene, or optionally substituted heteroarylene;
each $R_3$ is independently H, optionally substituted alkyl, C(O)OR, or C(O)NRR;
each R is independently H or optionally substituted alkyl;
each n is 0, 1, 2, or 3; and
each o is 0, 1, 2, or 3;
and pharmaceutically acceptable salts thereof.

2. The compound of claim 1, wherein each $R_2$ is independently optionally substituted alkenylene.

3. The compound of claim 2, wherein each $R_2$ is

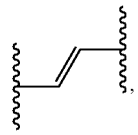

4. The compound of claim 2, wherein each $R_2$ is

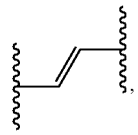

each $R_3$ is H, each n is 0, and each o is 2.

5. The compound of claim 1, wherein each $R_1$ is independently optionally substituted arylalkyl or optionally substituted heteroarylalkyl.

6. The compound of claim 5, wherein each $R_1$ is independently optionally substituted phenylalkyl or an optionally substituted (5-membered heteroaryl)alkyl.

7. The compound of claim 6, wherein each $R_1$ is independently

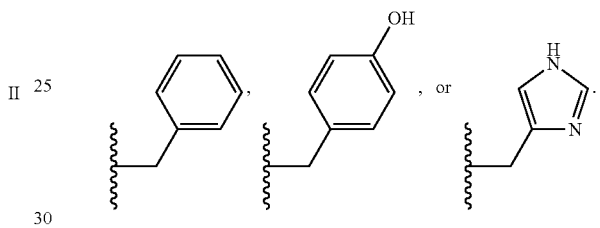

8. The compound of claim 1, wherein the compound is selected from the group consisting of:

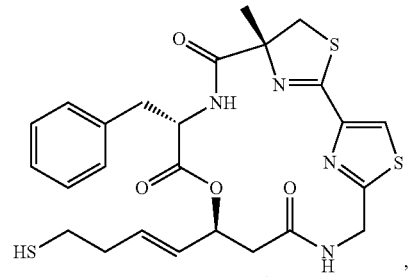

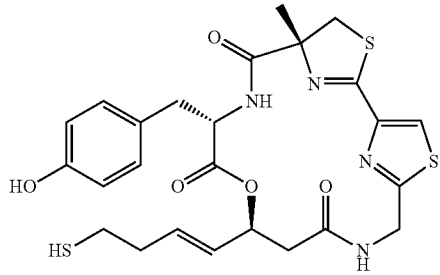

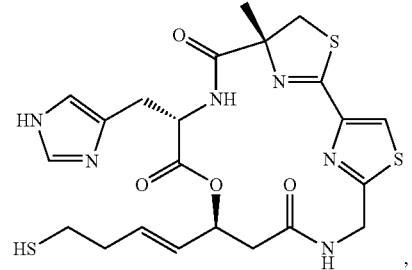

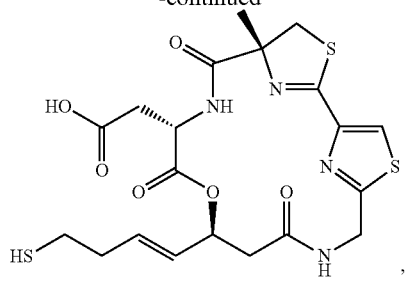
,
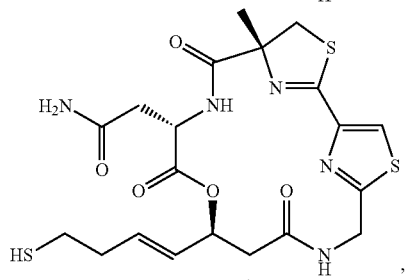
,
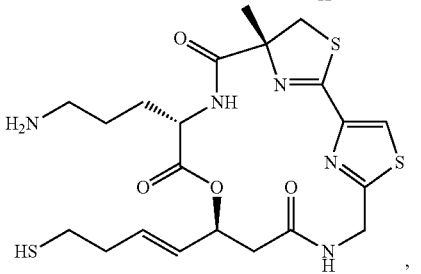
,
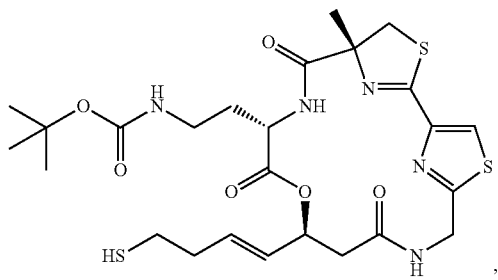
,

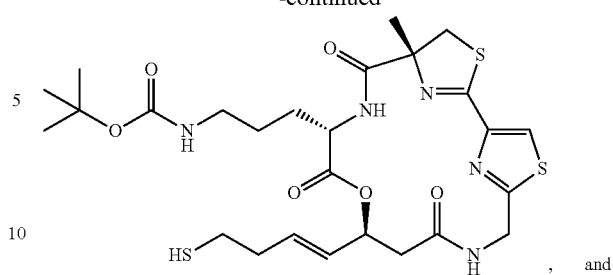
, and
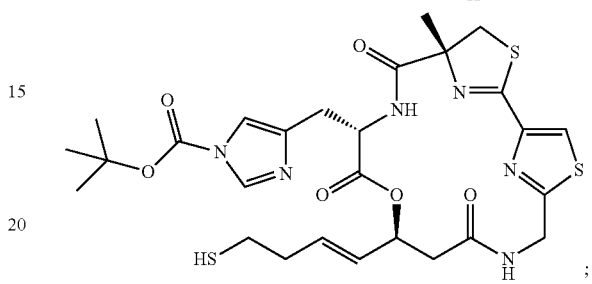
;

and pharmaceutically acceptable salts thereof.

9. A method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of a compound of claim 1, such that said subject is treated for said disorder;

wherein the cell proliferation related disorder or disease is solid tumor, colon cancer, breast cancer, bone cancer, brain cancer, osteosarcoma, neuroblastoma, colon adenocarcinoma, or an angiogenesis disorder.

10. The method of claim 9, wherein the disorder is solid tumor.

* * * * *